United States Patent
Blechman

(10) Patent No.: US 10,249,386 B2
(45) Date of Patent: Apr. 2, 2019

(54) ELECTRONIC HEALTH RECORDS

(71) Applicant: Elaine Blechman, Boulder, CO (US)

(72) Inventor: Elaine Blechman, Boulder, CO (US)

(73) Assignee: Prosocial Applications, Inc., Boulder, CO (US)

(*) Notice: Subject to any disclaimer, the term of this patent is extended or adjusted under 35 U.S.C. 154(b) by 16 days.

(21) Appl. No.: 14/588,304

(22) Filed: Dec. 31, 2014

(65) Prior Publication Data

US 2015/0213195 A1 Jul. 30, 2015

Related U.S. Application Data

(63) Continuation-in-part of application No. 13/418,768, filed on Mar. 13, 2012, which is a continuation-in-part of application No. 12/589,378, filed on Oct. 22, 2009, which is a continuation-in-part of application No. 10/853,488, filed on May 25, 2004, now abandoned, which is a continuation-in-part of (Continued)

(51) Int. Cl.
| | |
|---|---|
| G06Q 50/00 | (2012.01) |
| G16H 10/60 | (2018.01) |
| G06Q 50/22 | (2018.01) |
| G06F 19/00 | (2018.01) |

(52) U.S. Cl.
CPC .......... G16H 10/60 (2018.01); G06F 19/00 (2013.01); G06Q 50/22 (2013.01); G06Q 2220/10 (2013.01)

(58) Field of Classification Search
CPC ............................... G06Q 50/22; G06Q 50/24
See application file for complete search history.

(56) References Cited

U.S. PATENT DOCUMENTS

| 6,023,762 A | 2/2000 | Dean et al. |
| 6,024,699 A | 2/2000 | Surwit et al. |

(Continued)

OTHER PUBLICATIONS

Hall, Jon. Red Hat® Linux® for Dummies®, IDG Books Worldwide, Inc. Foster City, CA, 2000.

*Primary Examiner* — Joseph D Burgess
(74) *Attorney, Agent, or Firm* — Holzer Patel Drennan

(57) ABSTRACT

The system disclosed herein provides a method of populating an exclusively patient controlled record in a patient controlled electronic health record (PCHR) record repository, the method comprising: processing a request from a patient for a health information artifact; determining a supplier of the health information artifact; generating one or more information request templates required by the supplier of the health information artifact; generating an information request document using one or more of the information request templates; encrypting the information request document; sending the encrypted information request document to the supplier of the health information artifact; receiving the health information artifact; adding the health information artifact to the exclusively patient controlled record stored in the PCHR record repository; and controlling access of a user, human or machine, to the exclusively patient controlled record in the PCHR record repository based on (a) patient authorization of the user for future record access and (b) on consent from a registered device in response to the request of a patient-authorized user for current record access.

23 Claims, 26 Drawing Sheets

Related U.S. Application Data application No. 10/431,845, filed on May 8, 2003, now abandoned, which is a continuation-in-part of application No. 10/210,127, filed on Aug. 1, 2002, now abandoned.

(60) Provisional application No. 61/985,071, filed on Apr. 28, 2014.

(56) References Cited

U.S. PATENT DOCUMENTS

| | | |
|---|---|---|
| 6,612,985 B2 | 9/2003 | Eiffert et al. |
| 6,735,551 B2 | 5/2004 | Voegeli et al. |
| 7,016,877 B1 | 3/2006 | Steele et al. |
| 7,716,069 B2 | 5/2010 | Ulrich et al. |
| 7,849,400 B2 | 12/2010 | Ritter et al. |
| 7,856,366 B2 | 12/2010 | Dettinger et al. |
| 8,768,725 B2 * | 7/2014 | Lorsch .................. G06F 19/322 |
| | | 705/2 |
| 2002/0004727 A1 | 1/2002 | Knaus et al. |
| 2002/0010679 A1 | 1/2002 | Felsher |
| 2002/0013716 A1 | 1/2002 | Dunham |
| 2002/0032583 A1 | 3/2002 | Joao |
| 2002/0099568 A1 | 7/2002 | Turner |
| 2002/0099598 A1 | 7/2002 | Eicher, Jr. et al. |
| 2002/0165733 A1 | 11/2002 | Pulkkinen et al. |
| 2002/0184527 A1 | 12/2002 | Chun et al. |
| 2003/0140043 A1 | 7/2003 | Hotchkiss et al. |
| 2003/0236682 A1 | 12/2003 | Heyer |
| 2005/0075909 A1 * | 4/2005 | Flagstad ................ G06Q 10/10 |
| | | 705/3 |
| 2008/0059250 A1 | 3/2008 | Joao |
| 2014/0136236 A1 * | 5/2014 | Lee ...................... G06F 19/322 |
| | | 705/3 |

* cited by examiner

ELECTRONIC HEALTH RECORDS

CROSS-REFERENCE TO RELATED APPLICATIONS

This patent application is a non-provisional patent application based on U.S. provisional patent application Ser. No. 61/985,071 filed on Apr. 28, 2014 and is a continuation-in-part application of U.S. patent application Ser. No. 13/418,768 filed on Mar. 13, 2012, which is a continuation-in-part patent application of U.S. patent application Ser. No. 12/589,378 filed on Oct. 22, 2009, which is a continuation-in-part patent application of U.S. patent application Ser. No. 10/853,488 filed on May 25, 2004, which is a continuation-in-part patent application of U.S. patent application Ser. No. 10/431,845 filed on May 8, 2003, which is a continuation-in-part patent application of U.S. patent application Ser. No. 10/210,127 filed on Aug. 1, 2002, each of which is incorporated by reference herein.

FIELD

Implementations disclosed herein relate, in general, to information management technology and specifically to health records management systems.

SUMMARY

The patient-controlled electronic health record (PCHR) system disclosed herein provides for a method of populating an exclusively patient controlled record in a patient controlled electronic health record (PCHR) record repository, the method comprising: processing a request from a patient for a health information artifact; determining a supplier of the health information artifact; generating one or more information request templates required by the supplier of the health information artifact; generating an information request document using one or more of the information request templates; encrypting the information request document; sending the encrypted information request document to the supplier of the health information artifact; receiving the health information artifact; adding the health information artifact to the exclusively patient controlled record stored in the PCHR record repository; and controlling access of a user, human or machine, to the exclusively patient controlled record in the PCHR record repository based on (a) patient authorization of the user for future record access and (b) on consent from a registered device in response to the request of a patient-authorized user for current record access.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Other features, details, utilities, and advantages of the claimed subject matter will be apparent from the following more particular written Detailed Description of various embodiments and implementations as further illustrated in the accompanying drawings and defined in the appended claims.

BRIEF DESCRIPTION OF THE DRAWINGS

A further understanding of the nature and advantages of the present technology may be realized by reference to the figures, which are described in the remaining portion of the specification. In the figures, like reference numerals are used throughout several figures to refer to similar components. In some instances, a reference numeral may have an associated sub-label consisting of a lower-case letter to denote one of multiple similar components. When reference is made to a reference numeral without specification of a sub-label, the reference is intended to refer to all such multiple similar components.

DETAILED DESCRIPTION

Figure 1:
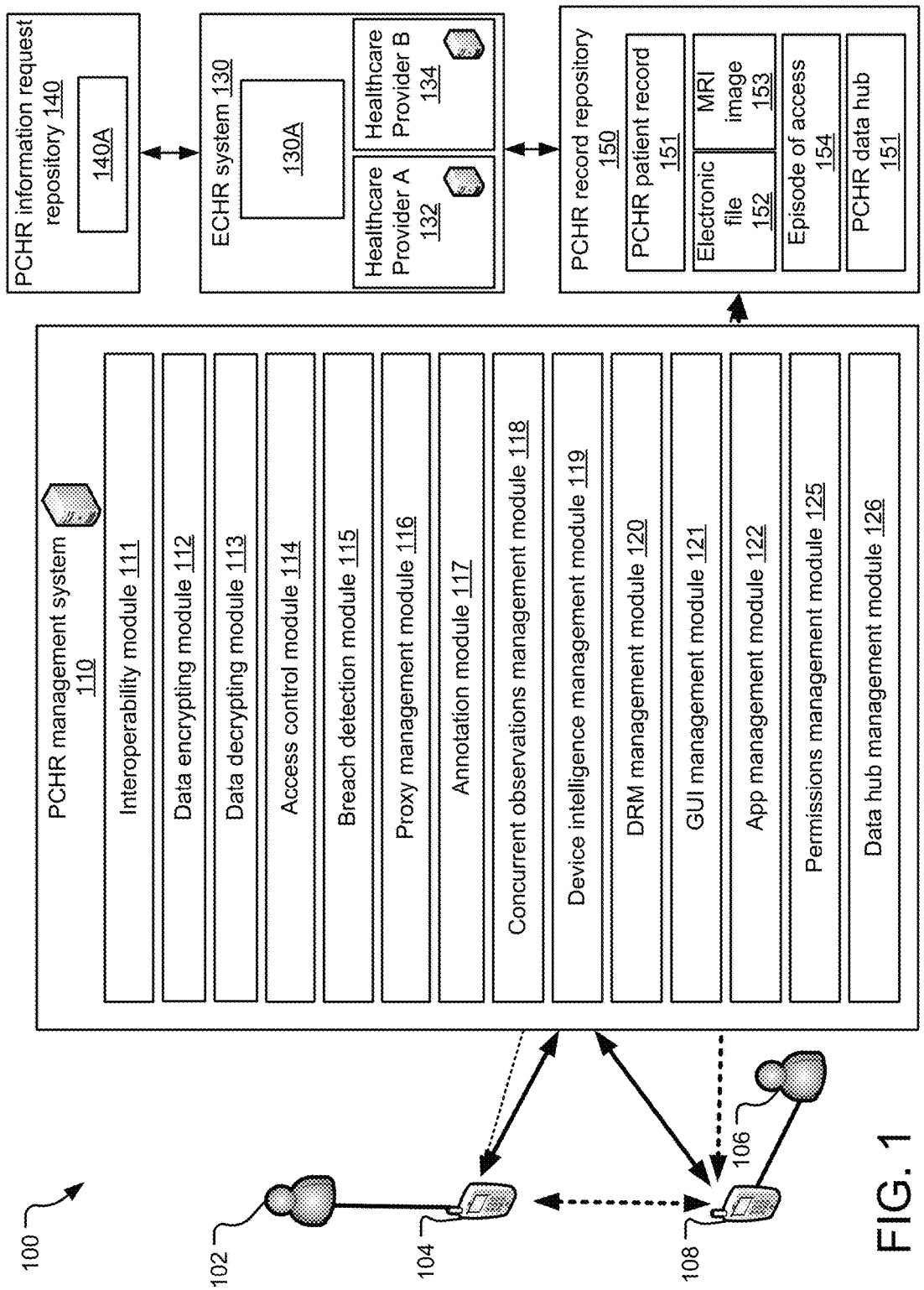
FIG. 1 illustrates an example block diagram representing an exclusively patient-controlled electronic health record (PCHR) system disclosed herein.

Few consumers of healthcare services in the U.S., may use personal computers and mobile phones, connected to the Internet, for exclusive control over transactions within and between the totality of their patient records lodged in the exclusively enterprise-controlled electronic health record (ECHR) systems of healthcare enterprises including professional practice offices, hospitals, urgent care centers, pharmacies, laboratories, radiology centers, and health insurance companies as well as skilled-nursing, assisted-living, rehabilitation, and long-term care facilities. Online patient portals, which offer glimpses of some information in some records in some ECHR systems, give consumers the illusion of control. Fragmented documentation of healthcare services in the insular ECHR systems of competing healthcare enterprises, largely inaccessible to consumers but subject to frequent illegitimate breaches, burden consumers who must physically transport their health records from one provider to another and cause needless, dangerous and costly errors by healthcare providers acting on inaccurate and incomplete patient information.

For example, a 2014 Commonwealth Fund report found that test results were unavailable at appointments for 23% of Medicare patients (more than in Australia, Canada, France, Germany, Netherlands, New Zealand, Norway, Sweden, Switzerland or the UK), so doctors order costly, duplicate tests. The U.S., therefore, remains near the bottom and Singapore is at the top in Bloomberg's 2014 annual ranking of countries with the most efficient health care, reflecting health care costs as a share of GDP and per capita income, as well as life expectancy. Healthcare enterprises, competing with each other for ownership of patient care and patient information, have resisted innovations in ECHR systems that would give consumers confidence in their ability to exercise exclusive remote control over health record transactions without adverse consequences from unauthorized breaches. A fundamental innovation in electronic health records is needed to overcome the dangerous, costly gaps in knowledge about patients characteristic of conventional, insular ECHR systems perpetuate.

An implementation of an exclusively patient-controlled electronic health record system (PCHR) disclosed herein enables a healthcare consumer to exercise exclusive control over her record in the PCHR system. Exclusive control would mean that healthcare consumers, and the representatives they appoint such as family members and healthcare professionals, would be the only ones who could enact, or authorize enactment of, electronic transactions within and between their PCHRs, such as transmission of MRI images from a radiology center to the office of an oncologist. The PCHR system enables the patient to establish a record in the PCHR system and to exclusively govern the import, storage, export, and access to data in their PCHRs including the exchange of data between their PCHRs and their records in the uncommunicative ECHR systems of their various healthcare providers. Another implementation of the PCHR system disclosed herein empowers the patient to exercise exclusive control over the PHCR record from a registered patient device as no ECHR system does. The patient uses her registered device to send to the record repository of the PCHR system, a digitally signed message controlling access by a user requesting access to her PCHR record, and to view an audit report from the system on her registered device describing resulting system behavior such as granting or denying the user access to the record. The PHCR system encrypts all patient data in storage on PCHR system servers and in transit between the PCHR system, registered devices, and external record systems such as ECHR systems. Thus, the security of data in patient records is maximized and the PCHR system is in compliance with government regulations and industry standards for operation of conventional ECHR systems.

Yet an alternative implementation of the PCHR system disclosed herein allows a patient to designate a series of patient proxies who, when registered patient devices are unresponsive, may send from their registered devices to the record repository of the PCHR system, digitally signed messages consenting to requests by users, even if previously authorized, for access to the patient record, and may view audit reports from the system on their registered devices describing system behavior such as granting or denying record access. For example, a patient can specify that if the patient's registered device does not respond to a request by an emergency responder for entry to the patient record, the PCHR record repository will, in turn, notify a patient proxy, such as the patient's husband, brother, and sister, each of whom may consent from their registered devices to patient record access by the emergency responder.

These and other implementations of the PCHR system disclosed herein are further illustrated by example implementations in the following figures and the related disclosure thereof.

FIG. 1 illustrates an example block diagram representing an exclusively patient-controlled electronic health record (PCHR) system 100 disclosed herein. The PCHR system 100 includes a PCHR management system 110 comprised of one or more modules for implementation of various functions. Such PCHR system 100 and PCHR management system 110 may be implemented on a computing system such as a server, a cloud based system, etc., that is communicatively connected to a network, such as the Internet, etc. A patient 102 may communicate with the PCHR management system 110 using a device 104, such as a cellphone, smartphone, computer, etc. The PCHR management system 110 is communicatively connected to one or more enterprise controlled health record (ECHR) systems 130, such as an ECHR system of a healthcare provider A 132, another ECHR system of a healthcare provider B 134, etc. Such healthcare providers may be hospitals, laboratories, healthcare practitioners, insurance companies, government organizations, etc.

The PCHR management system 110 is also communicatively connected to a PCHR information request repository 140, wherein the PCHR information request repository 140 stores as electronic templates, various forms that patients must submit when requesting copies of information from their patient records in the ECHR systems of one or more of the healthcare providers 132, 134 for population of their patient records in PCHR system 100. For example, the information request repository 140 may store as electronic templates the forms that the administrators of ECHR systems 130 and the administrators of the physical record rooms of healthcare providers 132, 134 require before handing over requested information to patients or transmitting requested information electronically to the PCHR system 100. Furthermore, the information request repository 140 may also store instructions about the format, data elements, encryption, transmission, and payment requirements for successful submission of information requests to ECHR systems 130 and healthcare providers 132, 134.

The PCHR management system 110 is also communicatively connected to a PCHR record repository 150 that stores patient records. The PCHR record repository 150 is implemented as a firewall protected data store where all communication with the PCHR record repository 150 is required to be encrypted by a particular encryption certificate. The PCHR data store 150 communicates with authenticated users of registered patient and patient proxy devices 104, 108, and with the PCHR management system 110 employing only encrypted communication methods. For example, the patient 102 must present credentials authenticating her identity, such as a passcode, biometrics, etc. before she can login to an app resident on her registered patient device 104 and access her patient record in the PCHR record repository 150. The app resident on the registered patient device 104 stores an encryption certificate used to send the access request of patient 102 to the PCHR record repository 150. Furthermore, the app resident on the registered patient device 104 also stores a decryption certificate used to decrypt the access confirmation from the PCHR record repository 150 and grant patient 102 access to her record in the PCHR record repository 150.

An interoperability module 111 is configured to send an information request from patient 102 to the administrator of ECHR system 130 requesting information stored in a record 130-A of patient 102. For example, the patient 102 may want to upload to her patient record 151 in PCHR record repository 150, a copy of the MRI image 153 that healthcare provider A 132 stored in patient record 130-A of the ECHR system 130. The information request repository 140 may store as electronic templates the forms that the administrator of ECHR system 130 requires before handing MRI image 153 on a CD to patient 102 or transmitting MRI image 153 electronically to a PCHR patient record 151 in PCHR record repository 150.

Upon initiation by patient 102 of the information request, the interoperability module 111 communicates with the information request repository 140 to determine the requirements of ECHR system 130 for submission of information requests, such as the last four digits of the patient's social security number.

Furthermore, the interoperability module 111 may reuse information available in the patient record 151 in PCHR record repository 150, such as the last four digits of the patient's social security number, to populate required fields in the information request form, leaving the patient 102 to supply information not available in the patient record 151 and to digitally sign a resulting information request document 140A. In one implementation, the interoperability module 111 offers patient 102 the choice between preparing and submitting the information request document 140A by herself or automated preparation and submission of the information request document 140A by PCHR system 100.

The interoperability module 111 prepares and submits to ECHR system 130 an encrypted information request document 140A in conformance with requirements of ECHR system 130 and of industry-standard protocols and government regulations for health information exchange between electronic health record systems such as PCHR system 100 and ECHR system 130. In one implementation, a data-encrypting module 112 encrypts the information request document 140A with a key that allows only an individual administrator of ECHR system 130 to decrypt the document. In this manner, the PCHR system 100 assigns accountability for the privacy and integrity of information request document 140A.

The interoperability module 111, after submitting to ECHR system 130 an encrypted information request document 140A, confirms that the administrator of ECHR system 130 received and decrypted the information request document and intends to fulfill the patient's request and the requirements of PCHR system 100 by sending to PCHR system 100 an encrypted message containing either a copy of or a link to the MRI image 153 stored in patient record 130-A of the ECHR system 130. After PCHR system 100 receives from ECHR system 130 an encrypted message containing either a copy of or a link to MRI image 153 stored in patient record 130-A of the ECHR system 130, a data decrypting module 113 decrypts the message and the interoperability module 111 confirms the authenticity of the sender and the integrity of the MRI image 153, stores the image in patient record 151 with tags detailing the source and original status of the image upon receipt, and notifies patient 102 about fulfillment of her information request.

The PCHR system 100 is configured to control access to the record repository 150 such that patients exercise exclusive control over access to the patient records therein. For example, once the PCHR management system 110, as requested by patient 102, updates her patient record 151 in the record repository 150 with MRI image 153 obtained from ECHR system 130, the access control module 114 restricts access to MRI image 153 and to other contents of patient record 151 to patient 102 and to users who patient 102 authorized with suitable permissions through permissions management module 125.

The PCHR management system 110 also includes an access control module 114 that controls access to the PCHR record repository 150 of the management system 110 consistent with user permissions authorized by the patient through the permissions management module 125. Each patient record in the record repository 150 is associated with registered devices of patients and patient proxies that communicate with the access control module 114. For example, record 151 of patient 102 is associated with the registered patient device 104. In one implementation, healthcare provider B 134, previously authorized by patient 102 to view MRI image 153, may access record 151 and view image 153 from his web-connected computer, only if patient 102 from registered patient device 104 consents to this episode of access 154 to record 151.

In such an implementation, an episode of access 154 to patient record 151 by healthcare provider B 134 is contingent upon a properly encrypted access consent message sent by registered patient device 104 to management system 110; a consent message sent to management system 110 that is improperly encrypted or comes from any other device or source does not meet the requirements for an episode of access 154 to patient record 151.

Yet alternatively, the management system 110 further includes a breach detection module 115 configured such that if the management system 110 receives a number of requests for access to patient record 151 that are improperly encrypted or come from sources other than registered patient device 104 and exceed a predetermined threshold, then breach detection module 115 may determine that an attempt for unauthorized access is underway. Alternatively, if the audit log of the access control module records an episode of access 154 to patient record 151 that lacks suitable patient-authorized permissions or that lacks consent from the registered device of the patient 104 or a patient proxy 106, then the breach detection module 115 may determine that an attempt for unauthorized access is underway.

Furthermore, the management system 110 is configured such that if the breach detection module 115 determines that an attempt for unauthorized access is underway, then the PCHR system 100 may alert the patient and patient representatives about the breach, send a complete encrypted copy of all contents of the patient record 151 to a storage destination designated by the patient 102, remove the patient record from the record repository 150, pending inquiry by an independent security analyst deny all future access to any patient record in the record repository 150 by the human user or machine associated with the potential breach, and transfer administrative control of the PCHR system 100 to a system administrator supervised by an independent security analyst.

The PCHR management system 110 also includes a proxy management module 116 that is configured to manage access to patient records by patient designated representatives or proxies. For example, the patient 102 may specify her spouse as a proxy such that the spouse may register his device with a device intelligence management module 119 and use his device to communicate with the system 110 when the patient 102 does not respond to messages sent by the system 110 to her device because of a faulty device or when the patient 102 cannot respond to the system 110 because she is incapacitated. Like the patient, proxies can use their registered devices to invoke the permissions management module 125 for authorization of users with record access permissions, to consent to patient record access at the moment a previously authorized user requests record access, and to respond to potential breaches. The patient may use the proxy management module 116 to designate a series of proxies who can register their devices for communication with the system 110, to change these designations in the future, and to specify the order in which the system 110 communicates with the registered devices of patient and proxies about matters such as requests for record access or potential breaches.

The proxy management module 116 distinguishes the architecture of the PCHR system 100 from that of all other electronic health record systems, which enable individuals unknown to the patient 102, such as administrators of a hospital's ECHR system 130, who may have conflicts of interest about matters such as record breaches, to exercise ultimate control over the patient record 130A.

The PCHR management system 110 also includes the permissions management module 125 that is configured to assist patients in managing the permissions of an individualized hierarchy of users. In the hierarchy are named individuals, each designated by the patient, and authorized with permissions including those related to role (e.g., record administrator, healthcare provider), content (e.g., all content, only diagnostic images), functions (e.g., all functions, only view and download diagnostic images online, receive messages requesting information stored in an ECHR system), time periods (e.g., until replaced by the patient, only the next 30 days), and means of access such as mobile- or web-connected computers, web services, and designated ECHR system (e.g., all means of access, only the ECHR system designated by the healthcare provider).

In one implementation, the permissions management module 125 is configured to create a hierarchy of permissions such that all users have permissions lesser than those of the patient or the patient's legal guardian or holder of medical power of attorney and a record administrator has permissions lesser than those of the patient and greater than those of all other users. In another implementation, the permissions management module 125 is configured to require users authorized with permissions on a patient record to be identified as individuals (e.g., Dr. Sam Smith), not as corporate healthcare enterprises (e.g., City Hospital), or as anonymous occupant roles in healthcare enterprises (e.g., radiologists at City Hospital). In yet another implementation, the permissions management module 125 is configured so that a record administrator may authorize a healthcare coordinator (with lesser permissions than the record administrator) to authorize healthcare providers (with lesser permissions than the healthcare coordinator). For example, the patient 102 uses the permissions management module 125 and the proxy management module 116 to designate her spouse as record administrator and proxy. When the patient 102 is hospitalized, her spouse designates a nurse practitioner employed by the hospital as care coordinator and proxy. Relieving the burdens of patient and spouse, the nurse practitioner uses her registered device to grant permissions (lesser than hers) to an on-call partner who is available when she is not and to healthcare professionals delivering services to patient 102 and she can use her device to regulate momentary record access by previously authorized users and respond to potential breaches.

The permissions management module 125 distinguishes the architecture of the PCHR system 100 from an ECHR system 130. The patient permissions management module 125 of the management system 110, endows the patient with the highest level of permissions for access to all contents of her record 151, enables a patient 102 to determine permissions for access by other users to contents of her record, and interactively controls the operations of every other module in the system 110 in respect to all contents of her record. The access control module 114, a GUI management module 121 and the interoperability module 111 depend on instructions from the permissions management module 125 for responses to human user and machine requests for access to patient record 151. If the patient 102 authorizes no users for access to the patient record 151, then the access control module 114 instructs the GUI management module 121 to bar all users from record access. If the audit log detects access to patient record 151 contrary to the instructions of the permissions management module 125, then the breach detection module 115 puts the PCHR system 100 into fail-safe mode and follows routines to notify the patient 102 about the breach, minimize the impact of the breach on patient 102, and prevent breaches of other patient records in the record repository 150.

In contrast, the business rules of a healthcare enterprise determine the role-based access permissions of enterprise employees, such as doctors and nurses, and of enterprise business associates, to all contents of a patient record 130A in an ECHR system 130 that the enterprise operates for business purposes. Enterprise business rules may also enable a patient 102 to access, and to authorize other users to access, some contents of her patient record 130A. Patient 102 cannot, however, access all contents of her patient record 130A, authorize users to access all contents of her record, or control access to her record by enterprise employees and business associates. In the event of a breach of a patient record 130A in ECHR system 130, enterprise management sets the policy for notification of patient 102, breach remediation and prevention, possibly without any changes to the operation of ECHR system 130.

The PCHR management system 110 also includes an annotation module 117 that is configured to permit selected users to affix permanent comments to the contents of record 151 without altering the contents. For example, after an office visit, healthcare provider-A sends an electronic clinical summary file to patient 102 that incorrectly lists her current medications and allergies. Patient 102 uploads the file to her record 151 and adds a comment that corrects these lists and is permanently affixed to the file. In one implementation, using the interoperability module 111, patient 102 can transmit the unaltered but annotated file to healthcare provider-A, requesting him to upload the corrected file to his ECHR 130. The annotation module 125 distinguishes the architecture of the PCHR system 100 from an ECHR system 130, in which the patient has limited access to contents of the patient record 130A, and has no opportunity to permanently affix corrections to record contents so as to avoid future healthcare safety errors such as administration of drugs that have previously caused the patient to suffer adverse reactions.

The PCHR management system 110 also includes a concurrent observation management module 118. In one implementation, the concurrent observation management module 118, in concert with the device intelligence management module 119, the proxy management module 116, and the permissions management module 125, allows users, with permissions for entry of their individual observations into the patient record from registered devices, to visualize the aggregate of all observations on their devices and to capture aggregate observations in an electronic file 152 suitable for storage in the patient record 151 of the system 110 and for transmission to the patient record 130A of an ECHR 130. For example, healthcare provider-A132 has prescribed an experimental drug to patient 102 requiring constant monitoring of the patient's vital signs to avoid serious side effects. Patient 102 has designated as proxies her husband, mother, and sister who take turns monitoring vital signs and entering data about blood pressure, heart rate, and temperature into the patient record 151 from their registered devices. At any time, they can visualize a graphic display of aggregate vital signs values, see alerts about values that require notification of healthcare provider-A132, and include an electronic file 152 graphically displaying aggregate vital signs values in an encrypted message to healthcare provider-A132 suitable for storage in patient record 130A of an ECHR 130. In another example, a child patient, his mother, father, and grandmother employ the concurrent observation management module 118 of the system 110 to independently monitor, jointly visualize, and share with specialists, observations of the child's aggressive, self-destructive and temper tantrum behaviors during episodes of drug-only, diet-only, and drug plus diet interventions.

The concurrent observation management module 118 distinguishes the architecture of the PCHR system 100 from mobile health apps, which enable several caregivers to enter their singular observations of a shared patient's vital signs into their mobile devices but not to visualize a graphic display of aggregate entries, to receive alerts when aggregate values require clinical intervention, to create an electronic file of the aggregate graphic display or to transmit the file in an encrypted message to a healthcare provider in a format suitable for inclusion in the patient record of an ECHR 130. The concurrent observation management module 118 also distinguishes the architecture of the PCHR system 100 from an ECHR system 130, which is not configured to capture, aggregate, display, and analyze non-standard, observational data from multiple patient and patient proxy sources.

The PCHR management system 110 also includes the device intelligence management module 119. The device intelligence management module 119 manages devices registered to the patient 102 and to the patient proxy 106 and the communication of such registered devices with the patient record 151 in the record repository 150. Such management of a registered patient device 104 and the registered patient proxy device 108 may include, for example, registration of devices, association of registered devices with patient records, generation of private keys by registered devices, communication between registered devices and the access control module 114, updating of device capabilities consistent with instructions from the permissions management module 125. In one implementation, if the registered device 104 of the patient 102 is lost or inoperable, the patient may access her record 151 by proving her identity to the device intelligence management module 119 with credentials such as biometric identifiers.

The PCHR management system 110 also includes a digital rights (DRM) management module 120. The DRM module 120 manages the rights to the contents of the patient record 151 in compliance with the instructions of patient 102 and the digital millennium copyright act (DMCA). A patient record 151 contains derivative content created by others. For example, the patient record 151 may include an MRI image ordered by a healthcare provider-A 132, given by, for example a radiology imaging center, to the patient 102 after MRI administration on a CD that includes the MRI image and relevant copyrights, and uploaded by patient 102 from the CD to the patient record 151 from a web-connected computer. The patient record 151 also contains original content created by the patient 102 and by users authorized by the patient 102 to enter data in the patient record 151. For example, the patient 102 has designated as proxies her husband, mother, and sister who take turns monitoring the patient's vital signs, create an encrypted electronic file 152 graphically displaying aggregate vital signs values, storing the encrypted electronic file 152 in the patient record 151. The DRM module 120 is configured to employ diverse technologies to control the secondary use of derivative and original patient record contents. In one implementation, for example, the patient 102 sends to healthcare provider-A 132 the encrypted electronic file 152, which the provider may store in patient record 130A of ECHR 130. To open the encrypted electronic file 152, both healthcare provider-A 132 and users of ECHR 130 must request from the system 110 transmission of a one-time passcode to a device registered with the device intelligence management module 119 of the system 110. Consistent with the authorization of patient 102, the system 110 sends a passcode for access to the encrypted electronic file 152 only to the registered device of healthcare provider-A 132. The many users other than healthcare provider-A 132 with access to the patient record 130A in ECHR 130, do not receive passcodes for access to the encrypted electronic file 152.

The PCHR management system 110 also includes a graphical user interface (GUI) management module 121 that controls access to the contents of patient record 151 in accordance with patient-authorized permissions for user access to the record from mobile devices, web-connected computers, etc. In one implementation, the GUI management module 121 is configured to permit patient 102, patient proxy 106, healthcare provider-A 132, and healthcare provider-B 132, consistent with their individual permissions, to access selected contents of the record 151. For example, the patient 102 as the owner of all contents of the record 151, can access all contents in the record; the patient proxy 106, consistent with patient-authorized permissions, can access all record contents added in the last 36 months; healthcare provider-A 132, consistent with patient-authorized permissions, can access all record contents marked as diabetes-related; healthcare provider-B 134, consistent with patient-authorized permissions, can access all record contents marked as cancer-related. In a related implementation, the GUI management module 121 is configured to permit patient 102, patient proxy 106, healthcare provider-A 132, and healthcare provider-B 132, consistent with their individual permissions, to add to the contents of record 151 by entering information into data fields, uploading attachments in industry-standard machine-readable formats (e.g., a radiology image in a DICOM (Digital Imaging and Communications in Medicine) format) and in non-standard formats (e.g., scanned image of a handwritten living will), and adding links to attachments stored in other systems.

In another implementation, the GUI management module 121 adds tags to entries into the record 151 by patient 102, patient proxy 106, healthcare provider-A 132, and healthcare provider-B 132, detailing the source of the entries and the original state of the entries so that no future user, including the patient, can either transform the original entries or question the integrity of the original entries. In yet another implementation, the GUI management module 121 is configured so that patients may compose and submit an industry-standard machine readable request for transmission of an MRI image 153 from ECHR system 130 to patient record 151 in record repository 150, automatically populating the record request with data stored in patient record 151 such as the patient's birth date and home address, etc. In a related implementation, the GUI management module 121 is configured so that the patient 102 may upload to her record 151 an MRI image 153 she received from ECHR system 130, associating the image with her signed request for MRI image 153 from ECHR system 130, so as to inform future users about the manner in which the patient obtained the MRI image.

The PCHR management system 110 also includes an App management module 122, which may be configured on a separate app server. In one implementation, the App management module 122 manages interactions with an application installed on the registered patient device 104 and on the registered proxy device 108 and facilitates communication of data between registered devices and the PCHR system 100 enabling patient 102 and proxy 106 to remotely exercise exclusive control over access to patient record 151.

The PCHR management system 110 also includes a data hub management module 126, which may be configured to display a data hub timeline referencing all contents of patient record 151 at the times they entered the record on the small screens of registered patient device 104 and registered proxy device 106. Patient record 151 is configured as a comprehensive health data hub for patient 102, storing information contents obtained from many sources by many methods over many years in the record repository 150. The patient 102 and her proxy 106 contribute to the contents of patient record 151 by entering data into their registered devices 104 and 108 and by uploading health information artifacts such as diagnostic images to patient record 151 from web-connected computers. The limited security and storage capacity of such devices makes storage of all contents of record 151 on these devices inadvisable. In one implementation, during a healthcare visit, the patient 102 shows the data hub timeline on her device to healthcare provider-B 134 so he can see the recent tests she has undergone and, through hyperlinks, get more details about each test.

In another implementation of the data hub management module 126, healthcare provider-B 134 asks patient 102 for permissions to access her record 151 from his web-connected computer and to view and download a recent MRI image he sees in the data hub timeline. The patient 102 uses her registered device 104 to authorize healthcare provider-B 134 with such permissions. Healthcare provider B-134 turns to his web-connected computer and begins to login to the record of patient 102 in the record repository 150. The access control module 114 sends a message to the registered device 104 of patient 102 indicating login initiation by healthcare provider-B 134. The patient 102 consents to login by healthcare provider-B 134 with the permissions she has just granted him. Healthcare provider-B 134 successfully logs into the patient record 151, downloads the MRI image to his web-connected computer, views the image in high resolution with the patient 102, and shares with her his impressions and recommendations.

The data hub management module 126 distinguishes the architecture and capabilities of the PCHR system 100 from an ECHR system 130. By offering a visual display from the patient device of the entire patient record with options for immediate authorization of user permissions and consent to their access from web-connected computers to specific record content, the data hub management module 126 represents an innovative solution for rapid retrieval of otherwise unavailable health information necessary for safe and high quality care.

Figure 2:
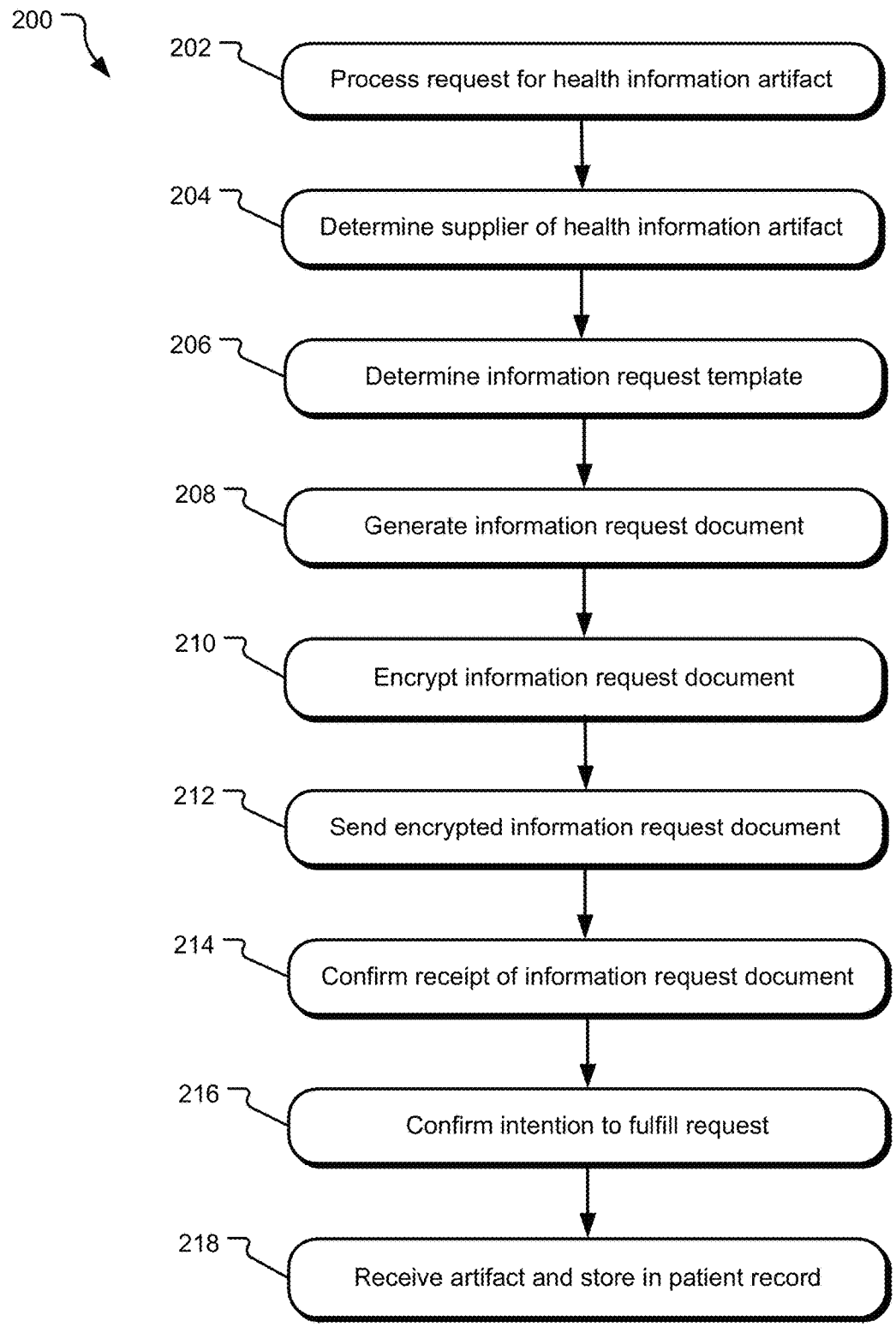
FIG. 2 illustrates an example flowchart of operations for entry of data into a patient record in an exclusively patient-controlled electronic health record (PCHR) system in response to receiving a request from a device that the patient has registered with the system.

FIG. 2 illustrates an example flowchart 200 of interoperability operations for populating a patient record in a patient-controlled health record system with health information stored in the patient record of an enterprise-controlled health record system. One or more of the operations of the flowchart 200 may be implemented on one server, on a collection of servers, a collection of servers, mobile devices, etc. An operation 202 processes a request for transmission of a health information artifact to the patient record in the record repository of a patient-controlled health record (PCHR) system. Such request for a health information artifact may be received from a patient, from a patient proxy, from a healthcare provider authorized by the patient to populate the patient record, etc. For example, after a hospital stay, a patient may request a hospital discharge summary, including aftercare recommendations. An operation 204 determines the healthcare enterprise capable of supplying patients with their health information artifacts, such as the requested hospital discharge summary. Such determination of the hospital discharge summary supplier may be based on analysis of the request for the hospital discharge summary, based on analysis of a healthcare enterprise database, etc.

An operation 206 determines the information request templates that patients must complete to request health information artifacts from healthcare enterprises. For example, such a template may specify the required content and structure of the form that a patient must submit to a hospital when requesting a discharge summary. The operation 206 may collect the information request templates required by various healthcare providers, make these available to patients in graphical user interfaces of mobile devices and web-connected computers, populate templates with required content such as the name of the patient, the patient's birthdate, the last four digits of the patient's social security number, etc., and prompt the patient to add necessary information such as the date of the hospital stay and to digitally sign the resulting information request document. An operation 208 uses the information request template to generate an information request document as required by the health information supplier, for example, as an industry-standard machine-readable electronic message that incorporates the digitally signed information request document and is addressed to the hospital's enterprise-controlled electronic health record system.

Subsequently, an operation 210 encrypts the information request document using open-source methods that do not require the health information supplier to employ any particular proprietary technology to decrypt the document.

An operation 212 sends the encrypted information request document to the health information supplier. An operation 214 confirms that the health information supplier, such as a hospital, has successfully received the information request document. An operation 216 confirms that the health information supplier, such as a hospital, has successfully decrypted the information request document and intends to fulfill the patient's request, such as for a hospital discharge summary. Subsequently, an operation 218 receives the requested health information artifact from the health information supplier, confirms the authenticity of the sender and the integrity of the artifact, and stores the artifact in the patient record with tags detailing the source and the original status of the artifact upon receipt. In a preferred implementation, all new and existing patient record contents are encrypted in transit and at rest, and are preserved in their original state preventing alteration by patients or patient-authorized users.

Figure 3:
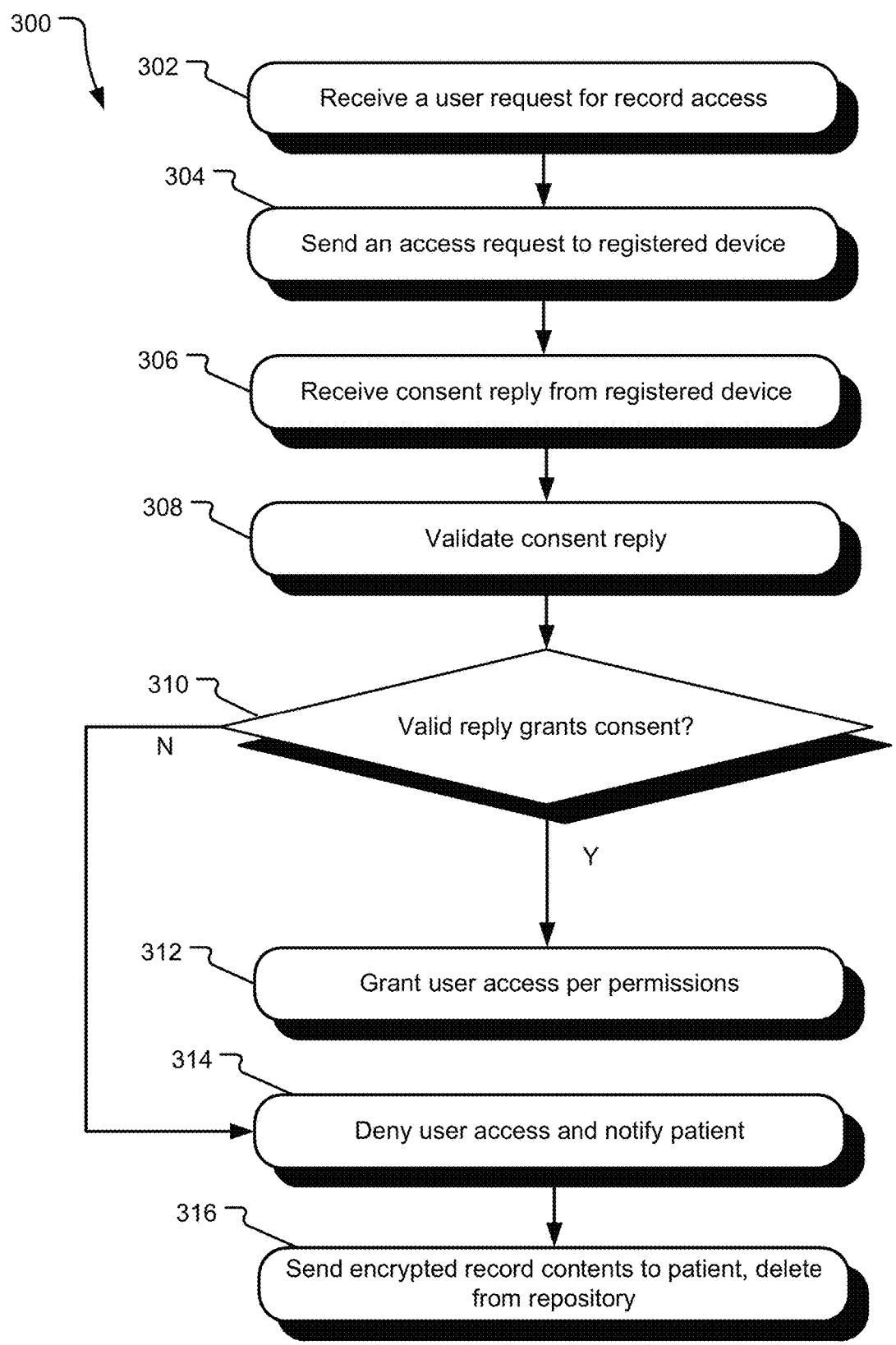
FIG. 3 illustrates an example flowchart of operations for patient consent to the request of a previously authorized user for access to the patient record in a PCHR system

FIG. 3 illustrates an example flowchart 300 of access control operations for a patient to grant consent when a previously authorized user requests access to the patient record in the record repository of a patient controlled health record (PCHR) system. Specifically, the operations confirm patient consent for access by a previously authorized user to a patient record that is stored in an encrypted record repository. An operation 302 receives a request for login to the record repository that an individual submits to the PCHR system through the user interface of a mobile device or web-connected computer.

In one implementation, an operation 304 authenticates the user's identity, determines the user's patient-authorized permissions and, if the access request comes from an authentic, patient-authorized user, sends a message to the registered device of the patient describing the access request and soliciting consent to the access request. The registered device of the patient may be a mobile phone. The access request message may be sent to the patient's registered device via a text message, an app based communication, etc. The patient may reply to the access request message, consenting to (or denying consent to) the access request via a text message, an app based communication, etc. An operation 306 receives the consent reply from the registered patient device. Such a protocol involving consent to record access issued by the registered patient device limits record access to users with both previous patient authorization and current patient consent. Furthermore, such a protocol limits record access by users who have achieved both prior patient authorization and current patient consent to patient-permitted content-, function-, and time-specific behaviors In one implementation, the registered patient device may include a private key and a digital signature in the consent reply. An operation 308 evaluates the private key and the digital signature received from the registered patient device. An operation 310 determines if the private key and the digital signature constitute a valid consent reply. A valid consent reply that grants current access to the previously authorized user, serves to authenticate the user requesting access. An operation 312 grants the authenticated user's request for access to the patient record governed by patient-authorized content-, function-, and time-specific permissions. In one implementation of operation 312, the authenticated user logs into the user interface of the patient record, which decrypts and displays record contents consistent with user permissions.

If the operation 310 determines that a consent reply is invalid or if a valid consent reply denies current access to a previously authorized user, an operation 314 denies the user request for access to the patient record. Additionally, the operation 314 may also send a message to the registered patient device reporting validation or invalidation of the consent reply and granting or denial of user access. Additionally, in one optional patient-selected implementation, upon determination of an invalid consent reply, an operation 316 sends encrypted files containing all contents of the patient record to the patient and deletes record contents from the record repository.

Figure 4:
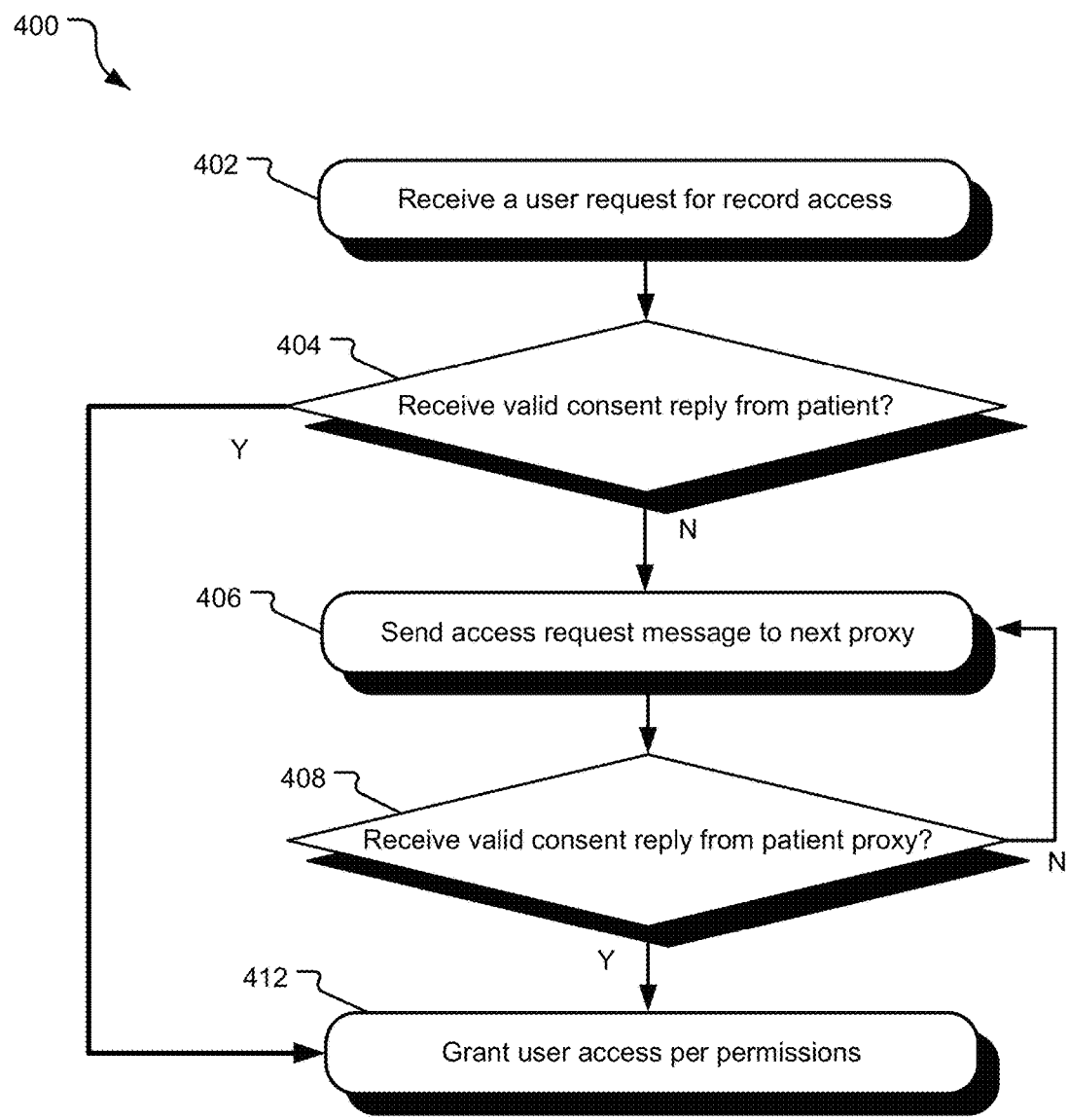
FIG. 4 illustrates an example flowchart of operations for patient authorization of a user for future access to the patient record in a PCHR system.

FIG. 4 illustrates an alternative example flowchart 400 of access control operations for a patient representative or proxy to grant consent when a previously authorized user requests access to the patient record in the record repository of a patient controlled health record (PCHR) system. An operation 402 receives a request for login to the record repository that an individual, who may be a healthcare provider, submits to the PCHR system through the user interface of a mobile device or web-connected computer. An operation 404 authenticates the user's identity, determines the user's patient-authorized permissions and, if the access request comes from an authentic, patient-authorized user, sends a message to the registered device of the patient describing the access request and soliciting consent to the access request.

If operation 404 results in the return of a valid consent reply from the patient device, an operation 412 grants the user's access request as per patient-authorized permissions. If operation 404 results in no response from the patient device, an operation 406 sends a message to the registered device of the next patient proxy in the patient-determined hierarchy. If operation 406 results in the return of a valid consent reply from the device of the next patient proxy, then the operation 412 grants the user's access request as per patient-authorized permissions. If operation 406 results in no response from the patient device, an operation 408 sends a message to the registered device of the second patient proxy in the patient-determined hierarchy. If operation 408 results in the return of a valid consent reply from the device of the second patient proxy, then the operation 412 grants the user's access request as per patient-authorized permissions. If operation 408 results in no response from the patient device, an operation 410 sends a message to the registered device of the second patient proxy in the patient-determined hierarchy, and so on until all patient proxy options are exhausted. In a preferred implementation, when all available patient and patient proxy devices are unresponsive, a "break-the-glass" option enables users to access a limited subset of record contents that the patient previously approved in case of emergency. In yet another implementation, the patient or proxy may authorize a class of users who may immediately invoke the "break-the-glass" option, such as state-licensed urgent care centers, upon presentation of credentials.

The operations of the flowchart 400 facilitate access to a patient record by authenticated users and by unauthenticated emergency responders despite the unavailability of a patient or the unresponsiveness of the registered patient device. For example, the patient may specify her spouse to be the next patient proxy and her son to be the second patient proxy, these patient proxies may register their devices with the PCHR system, which may provision the registered patient proxy devices with private key and a digital signature capabilities.

Figure 5:
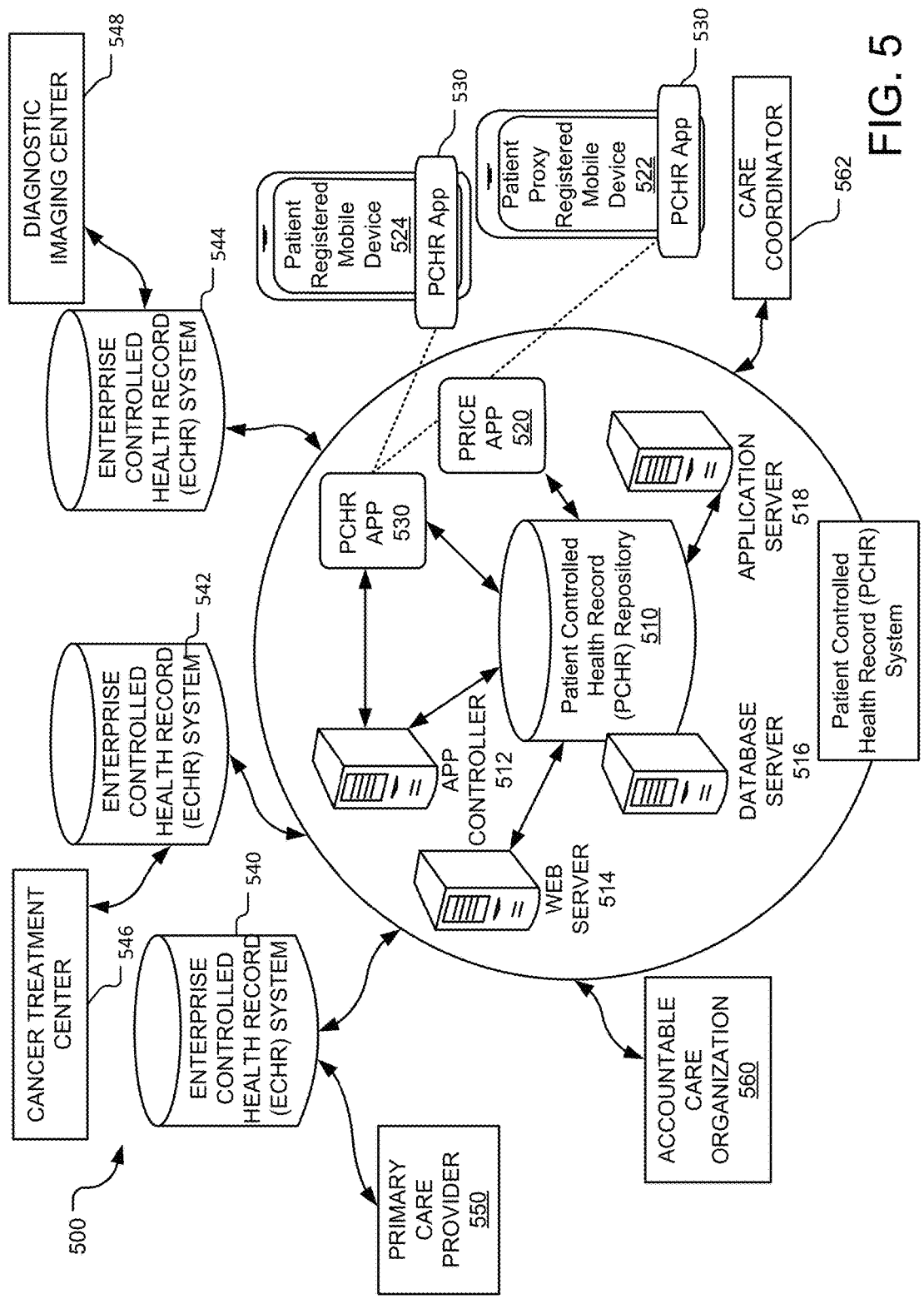
FIG. 5 is an example block diagram of a patient-controlled electronic health record (PCHR) system for enabling patients to create PCHR patient records and to exclusively control management of the PCHR patient records.

FIG. 5 is an example block diagram of a patient controlled electronic health record (PCHR) system 500 for enabling patients to create PCHR patient records and to exclusively control management of the PCHR patient records. An implementation of the PCHR system 500 is centered on a PCHR repository 510 that is firewall enabled and encrypts contents of patient records at rest during storage and in transit during exchange with external record systems. The PCHR repository 510 communicates with a PCHR app controller 512 that manages communication of the PCHR repository 510 with apps stored on various user devices. A web server 514 manages web-based communication with the PCHR repository 510. The PCHR repository 510 may be stored on a database server 516 that may be a cloud based database server.

The App controller 512 communicates with one or more PCHR apps 530 based on various user devices. In one implementation, the PCHR apps 530 are configured to store a private key and or a digital certificate that is required to communicate with the PCHR repository 510. The PCHR repository 510 is also configured to use an application server 518 to implement one or more of these services.

Additionally, the system 500 also includes a price app 520 that may be installed on a registered patient device and configured to engage in private comparison shopping on the patient's behalf, creating a report that compares prices and features for recommended healthcare services and products that conform to provider specifications. For example, a provider recommends a costly service or product (e.g., a hip replacement) to the patient who enters, with help from the provider, specifications for the hip replacement procedure into the price app together with patient preferences (e.g., preferred geographic region for the procedure). Based on searches of databases maintained by nonprofit, academic, and government organizations, the price app compares orthopedic surgeons who perform hip replacements that fit provider specifications and patient preferences on their prices for the procedure and their qualifications (e.g., number of such procedures performed, related residency and board certification, conflicts of interest). In one implementation, after a patient-authorized provider enters specifications for the recommended hip replacement procedure into the PCHR patient record, the price app senses the recommendation and seeks patient approval to proceed with the comparison-shopping report.

The system 500 provides for the PCHR repository 510, governed by patient permissions, to communicate with the record repositories of various enterprise controlled health record (ECHR) systems 540, 542, 546, etc. For example, the cancer treatment center 546 may maintain a record for the patient in the ECHR record repository 542; a diagnostic imaging center 548 may maintain a record for the patient in the ECHR record repository 544; a primary care provider 550 may maintain a record for the patient in the ECHR record repository 540. The system 500 allows a patient to use a PCHR app 530 to request from healthcare enterprises 546, 548, and 550 copies of health information artifacts that are located in her records in ECHR record repositories 542, 544, and 540 for transmission to her patient record in PCHR repository 510. Conversely, the system 500 allows healthcare enterprises 546, 548, and 550 to contact the patient via the PCHR system and request that she consent to sending copies of health information artifacts located in her record in the PCHR repository 510 to ECHR record repositories 542, 544, and 540. Furthermore, the system 500 allows healthcare providers who are unaffiliated with large healthcare enterprises and who lack ECHR systems, such as an accountable care organization 560 and the care coordinator 562, to access the patient record in the PCHR repository 510 from mobile phones and web-connected computers, given prior patient authorization and current patient consent. For example, when the patient-authorized care coordinator 562 attempts to login to the patient record in the PCHR repository 510, the system 500 sends a message to the PCHR app 530 on a registered patient device 522, 524, describing the access request and soliciting consent. If the patient consents, the system 500 grants record access to the care coordinator governed by patient-authorized permissions.

Figure 6:
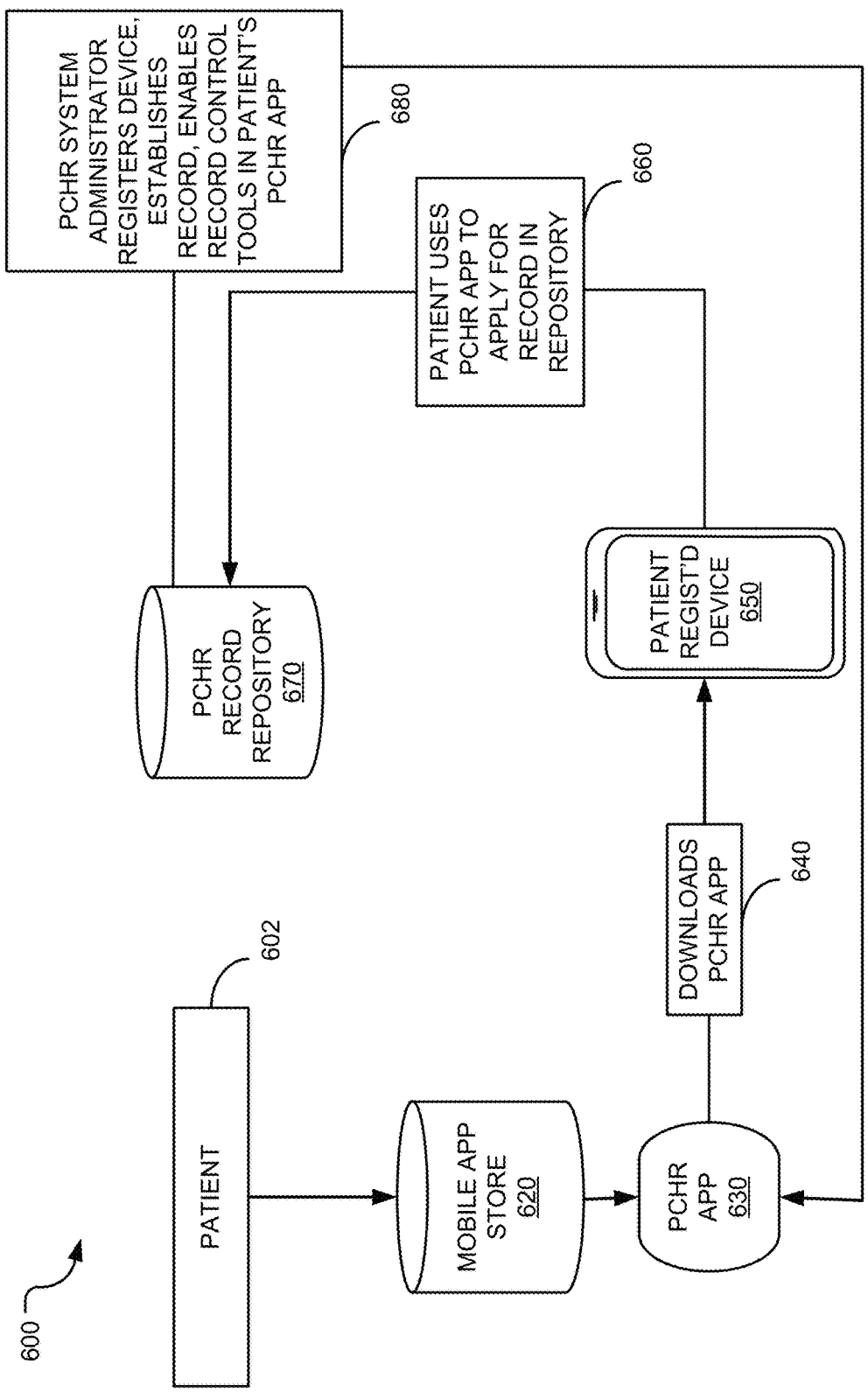
FIG. 6 is an example block diagram illustrating operations for patients to register devices from which they control their records in a PCHR system.

FIG. 6 is an example block diagram 600 illustrating operations for a patient to apply for a record in a PCHR record repository 670 and register a device that will control access to the PCHR patient record. For example, a patient 602 downloads 640 from a mobile app store 620 a PCHR app 630 to a mobile device 650. Subsequently, the patient on the device 650 uses the PCHR app 660 to establish a patient record in the PCHR record repository 670. An administrator 680 of the PCHR system registers the patient device 650 and enables patient 602 to control access to her patient record in the PCHR record repository 670 from the PCHR app 630 on her registered patient device 650.

Figure 7:
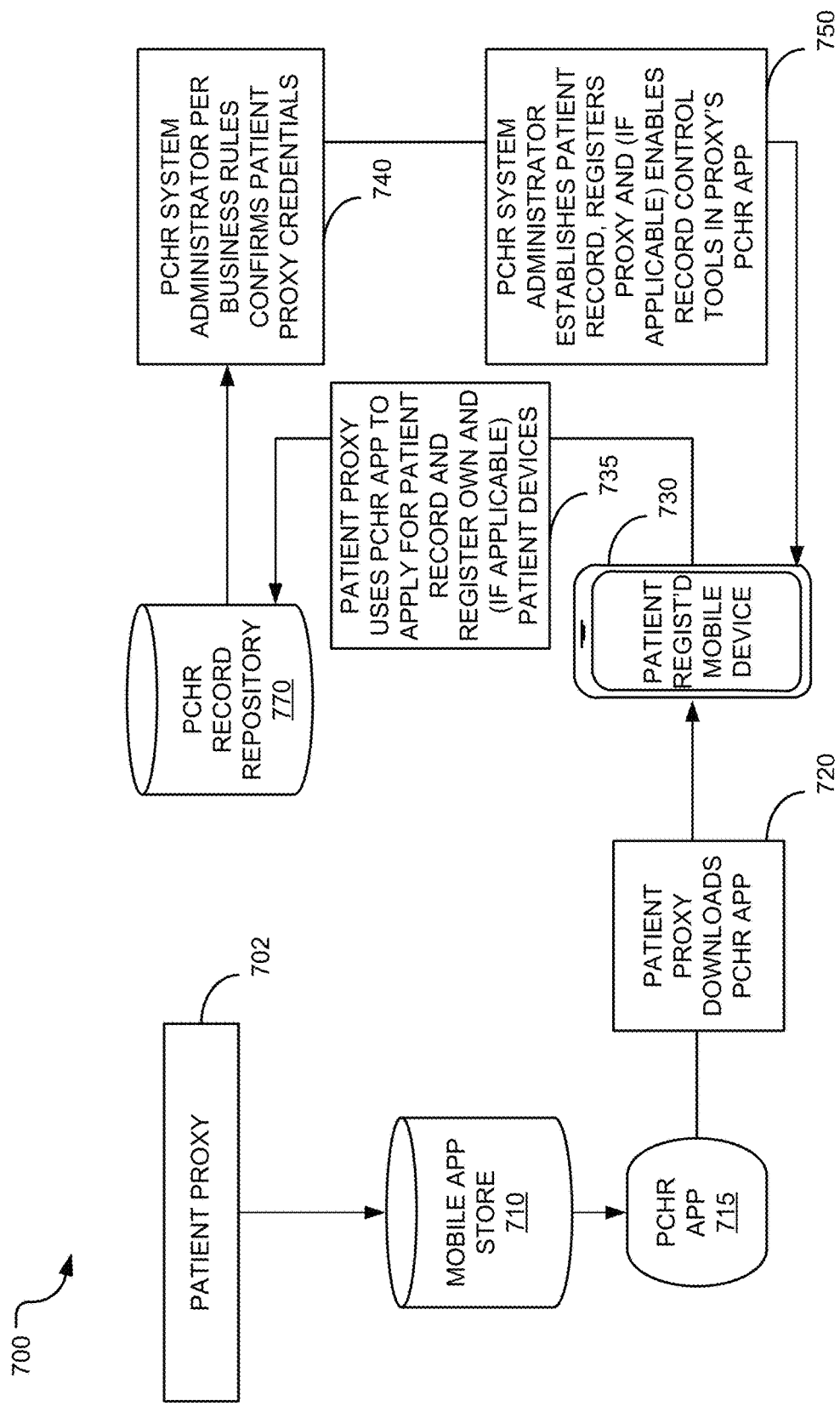
FIG. 7 is an example block diagram illustrating operations for patient representatives to register devices from which they control patient records in a PCHR system.

FIG. 7 is an example block diagram 700 illustrating operations for a patient representative or proxy to apply for a patient record in the PCHR record repository 770 and register a device that will control access to the PCHR patient record. In one implementation, a patient proxy, 702 for example, downloads 720 from a mobile app store 710 a PCHR app 715 to his mobile device 730. Subsequently, the patient proxy uses the PCHR app 715 on his device 730 to establish a patient record in the PCHR repository 770. An administrator 740 of the PCHR system registers the patient proxy device 730 and enables patient proxy 702 to control access to the patient record in a PCHR repository 770 from the PCHR app 715 on his registered patient proxy device 730. An administrator 750 may use various business rules 740 to confirm the authority of the patient proxy to establish and control access to the patient record. In another implementation, for example, the patient proxy who establishes the PCHR patient record and registers his device to control access to the record is the father of a child with cerebral palsy. Subsequently, other patient proxies who take turns in caregiving with the father, the child's mother, grandmother, and grandfather, may register their devices to control access to the child's PCHR patient record.

Figure 8:
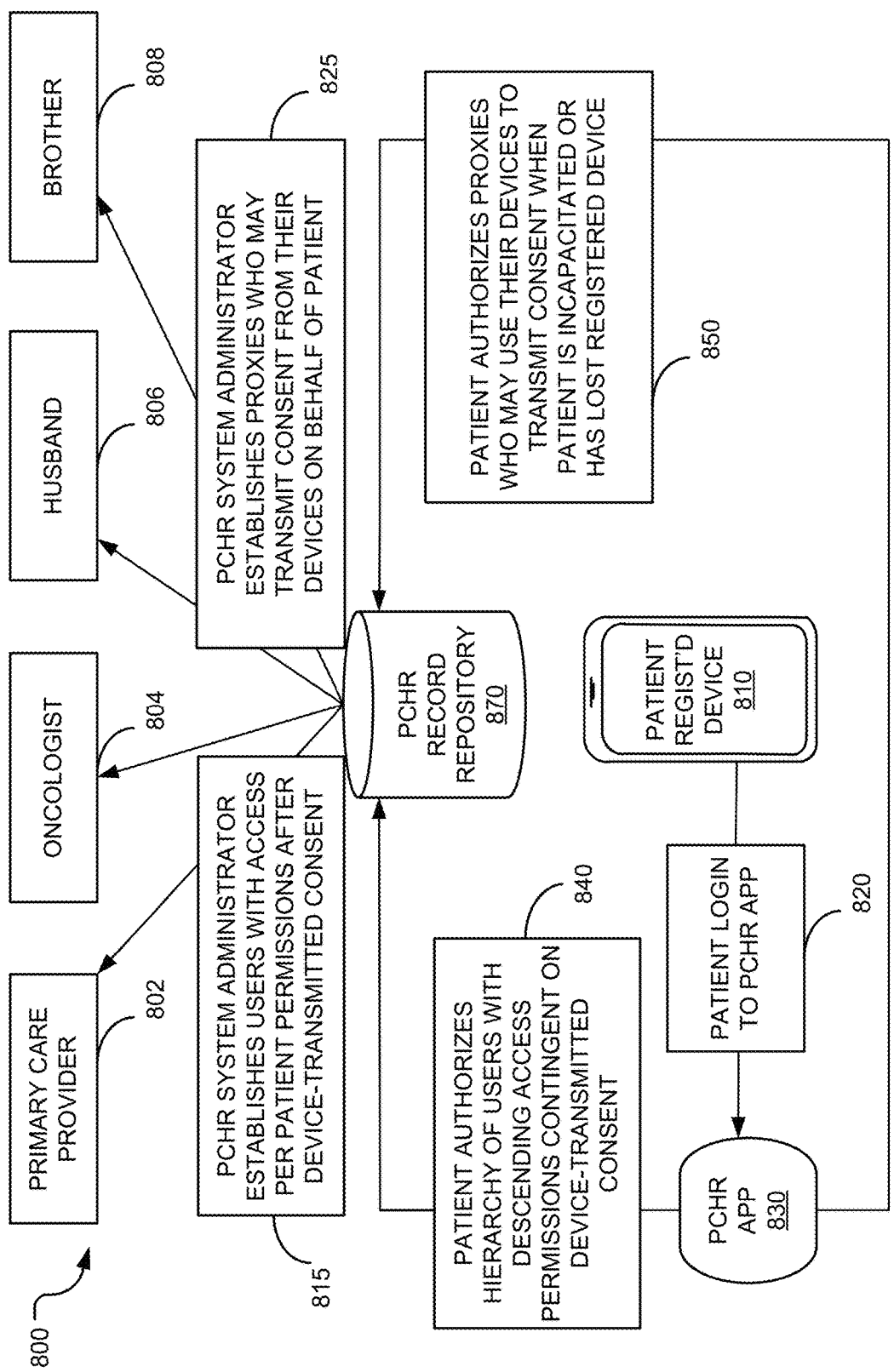
FIG. 8 is an example block diagram illustrating operations for patients to establish patient proxies who may consent from their registered devices, to requests by previously authorized users for patient record access in a PCHR system and for participants to establish users with access per patient permissions after device transmitted consent.

FIG. 8 is an example block diagram 800 illustrating operations for a patient to login 820 to a PCHR app 830 on a registered patient device 810, authorize 840 a hierarchy of users 802 and 804 with descending permissions for access to the patient record in a PCHR record repository 870 as subsequently established by a PCHR system administrator 815.

Alternatively, example block diagram 800 also illustrates operations for a patient to login 820 to the PCHR app 830 on the registered patient device 810, and authorize 850 a set of patient proxies 806 and 808 who may transmit consent to record access from their registered patient proxy devices 850 when the patient is incapacitated or the registered patient device is lost or stolen as subsequently established by a PCHR system administrator 825.

Figure 9:
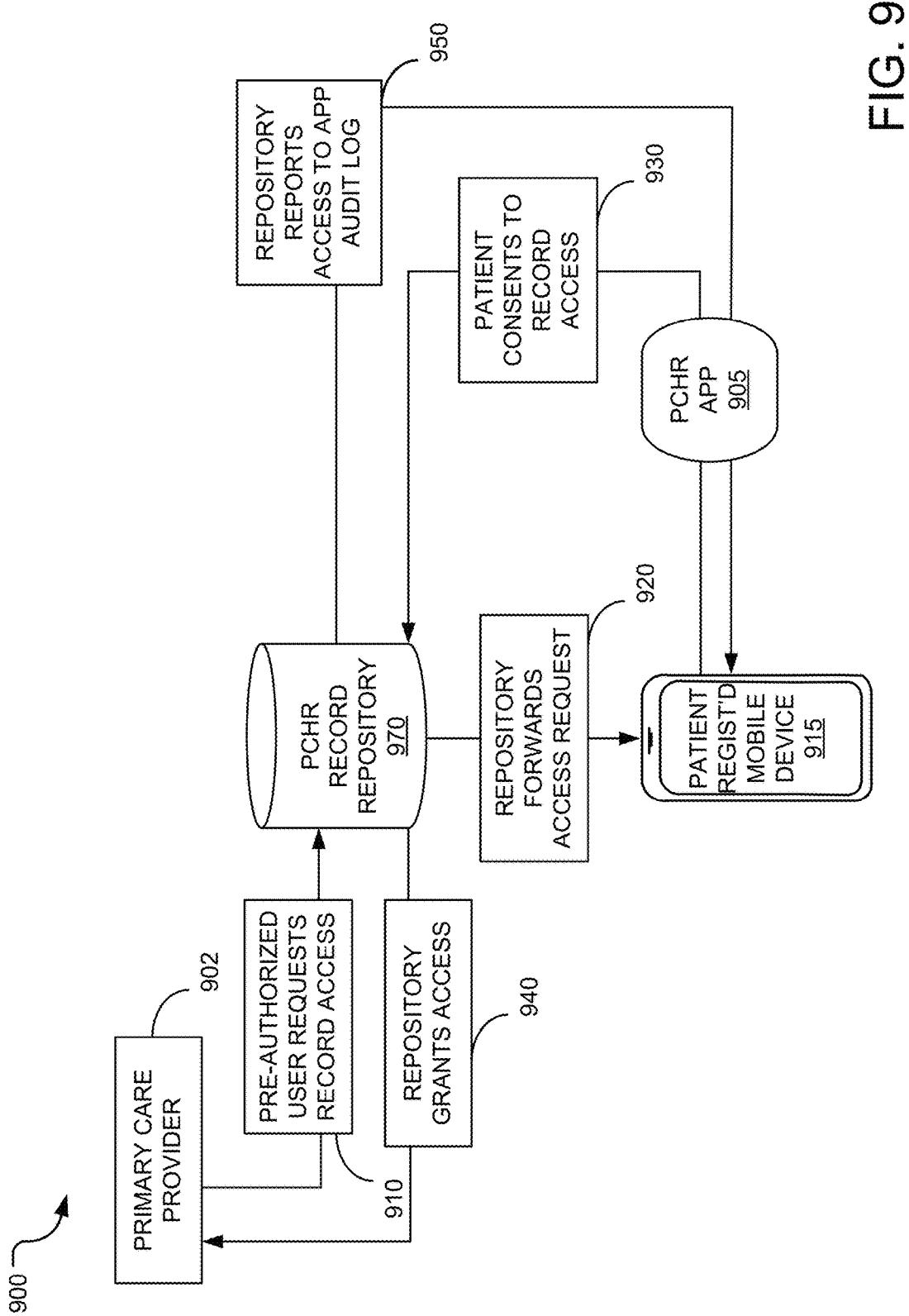
FIG. 9 is an example block diagram illustrating operations for communication between the PCHR record repository and the registered device of a patient, resulting in the patient consenting to a request for record access by a previously authorized user.

FIG. 9 is an alternative example block diagram 900 illustrating operations for allowing a patient to consent, when a previously authorized user requests access to the patient record in a PCHR record repository 970. For example, a year ago, the patient may have authorized a primary care provider 902 to access her patient records in the PCHR record repository 970. Today, primary care provider 902 requests access 910 to the patient record by attempting to login to the PCHR system 900 from his web-connected computer. In response to the request from the provider 902, the PCHR record repository 970 forwards 920 the access request 910 to a PCHR app 905 resident on registered patient device 915. If the patient, from the PCHR app 905, consents 930 to the access request 910, the PCHR record repository 970 grants access 940 to the patient record consistent with previously patient-authorized user permissions and records 950 details of the access episode in the audit log of the PCHR app 905.

Figure 10:
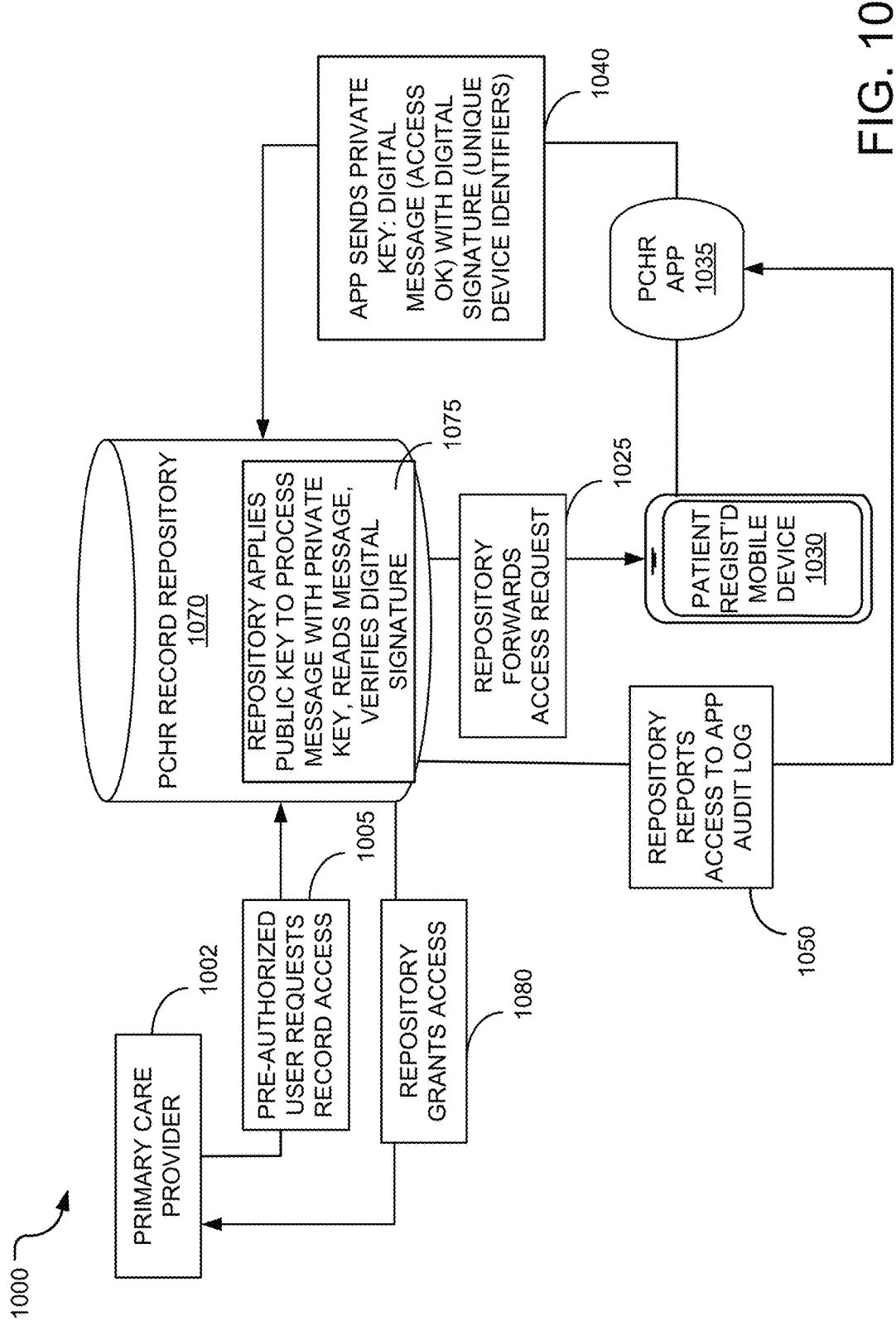
FIG. 10 is an example block diagram illustrating operations for a registered patient device to send to the PCHR record repository a digitally signed message consenting to patient record access by a previously authorized user and resulting in an audit report confirming access.

FIG. 10 is an example block diagram 1000 illustrating operations for encrypted communication of patient consent from a registered patient device to a PCHR record repository 1070. For example, a year ago, the patient may have authorized primary care provider 1002 to access her patient records in the PCHR record repository 1070. Today, primary care provider 1002 requests access 1005 to the patient record by attempting to login to the PCHR system from his web-connected computer. In response to the request from the provider 1002, the PCHR record repository 1070 may forward 1025 the access request 1005 to an app 1035 resident on a registered patient device 1030. If the patient, from the PCHR app 1035, consents to the access request 1005, the PCHR app 1035 may send an encrypted, digitally signed access consent message 1040 to the PCHR record repository 1070, which decrypts the message and verifies a digital signature 1075, before granting access 1080 to the patient record consistent with previously patient-authorized user permissions and records 1050 details of the access episode in the audit log of the PCHR app 1035.

Figure 11:
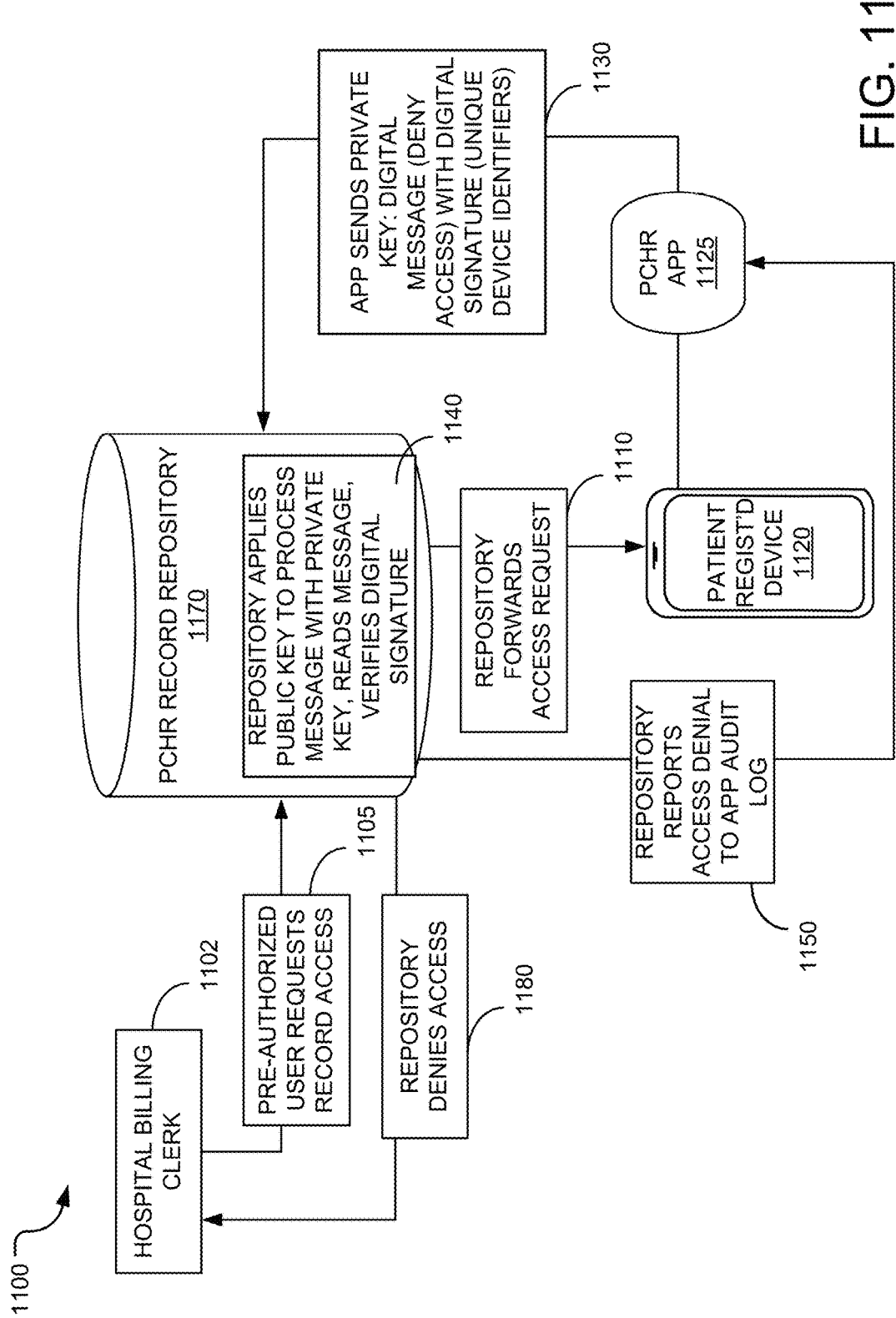
FIG. 11 is an example block diagram illustrating operations for a registered patient device to send to the PCHR record repository a digitally signed message denying patient record access by a previously authorized user and resulting in an audit report confirming denial of access.

FIG. 11 is an example block diagram 1100 illustrating operations for encrypted communication of patient denial of consent from a registered patient device to the PCHR record repository 1170. For example, a month ago, the patient may have authorized a hospital billing clerk 1102 to access her patient records in the PCHR record repository 1170. Today, hospital billing clerk 1102 requests access 1105 to the patient record by attempting to login to the PCHR system from her mobile tablet. In response to the request from billing clerk 1102, the PCHR record repository 1170 may forward 1110 the access request 1105 to an app 1125 resident on a registered patient device 1120. If the patient, from the app 1125, denies consent for access, the app 1125 may send an encrypted, digitally signed consent denied message 1130 to the PCHR record repository 1170, which decrypts the message and verifies a digital signature 1140, before denying access 1180 to the patient record and records 1150 details of the access request and denial in the audit log of the app 1125.

Figure 12:
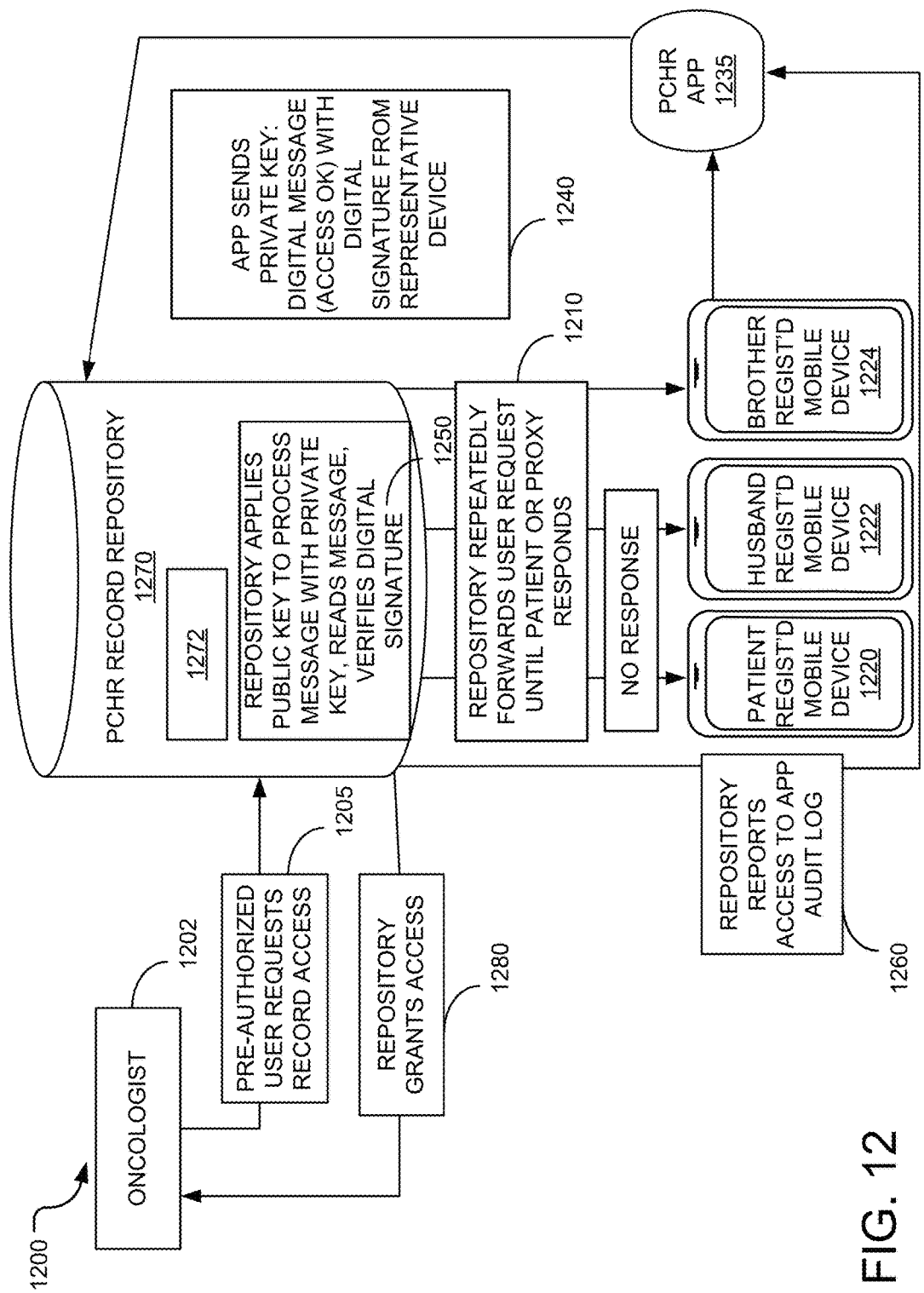
FIG. 12 is an example block diagram illustrating operations for the devices of a series of patient representatives, when the registered patient device is unresponsive, to send to the PCHR record repository digitally signed messages controlling patient record access by previously authorized users and resulting in audit reports of access

FIG. 12 is an example block diagram 1200 illustrating operations for a patient proxy to consent to patient record access when the registered patient device is unresponsive. For example, a week ago, the patient may have authorized an oncologist 1202 to access her patient record 1272 in the PCHR record repository 1270. Today, oncologist 1202 requests access 1205 to patient record 1272 by attempting to login to the PCHR system from a hospital computer workstation. In response to the request from oncologist 1202, the PCHR record repository 1270 repeatedly forwards 1210 the access request 1205 to a PCHR app 1235 resident on a series of registered patient and patient proxy mobile devices 1220, 1222, 1224, until the patient's brother from the PCHR app 1235 resident on his device 1224 sends an encrypted, digitally signed access consent message 1240 to the PCHR record repository 1270, which decrypts the message and verifies the digital signature 1250, before granting access 1280 to the patient record 1272 consistent with previously patient-authorized user permissions and documents details of the access episode in the audit log 1260 of the PCHR app 1235.

Figure 13:
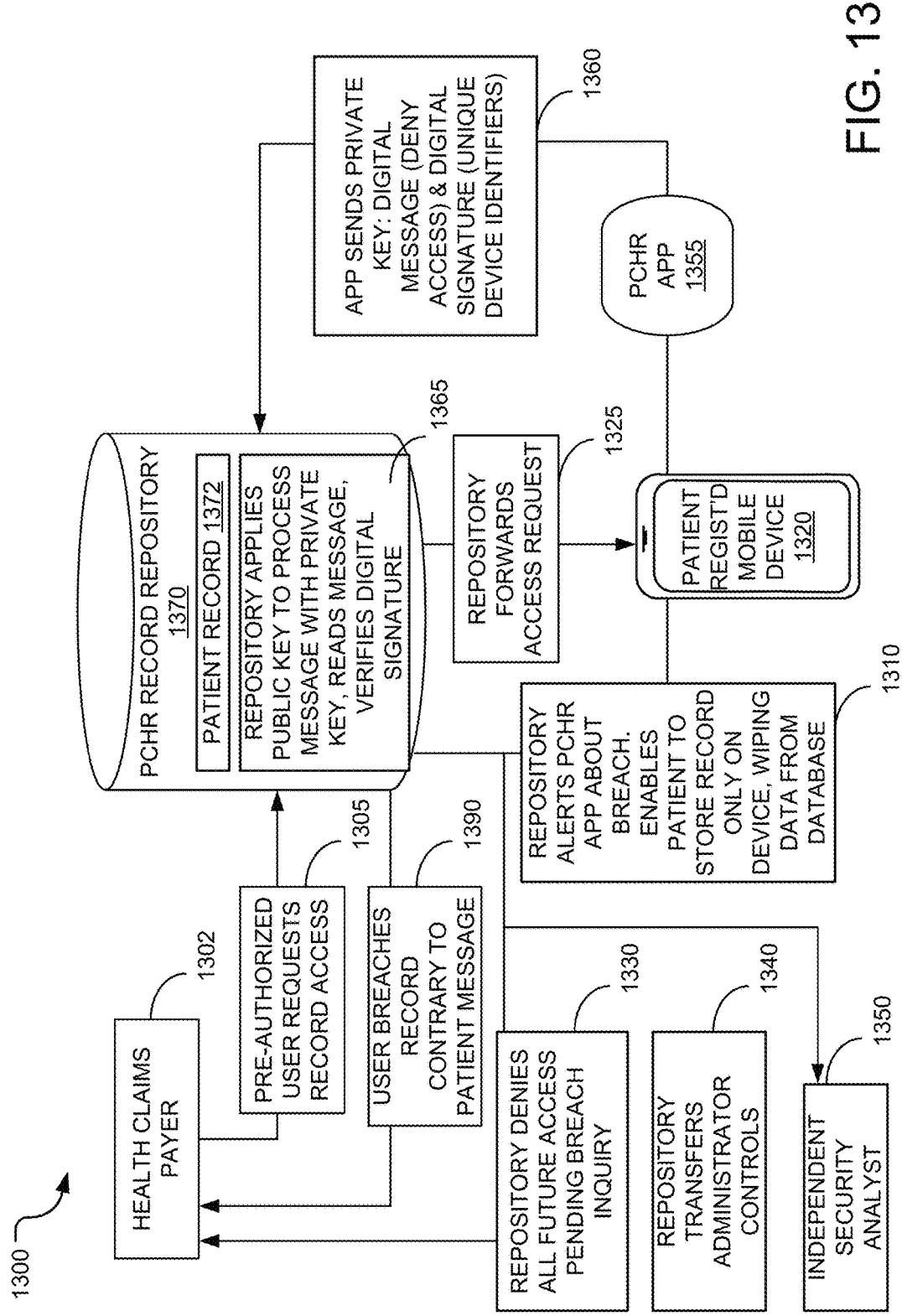
FIG. 13 is an example block diagram illustrating operations of the PCHR system after the record repository grants access to users attempting entry, contrary to messages from registered devices of patients or proxies, resulting in breaches of patient records.

FIG. 13 is an example block diagram 1300 illustrating exclusive patient control over patient records in the PCHR record repository. Specifically, the block diagram 1300 illustrates breach detection, notification, and remediation in a PCHR system. Thus, the components illustrated in the block diagram 1300 allow establishing exclusive patient control over their records in a PCHR record repository 1370. For example, 18 months ago, the patient may have authorized health claims payer 1302 to access her patient record 1372 in the PCHR record repository 1370. Today, a clerk employed by health claims payer 1302 requests access 1305 to the patient record 1372 by attempting to login to the PCHR system from his laptop. In response to the request from health claims payer 1302, the PCHR record repository 1370 may forward 1325 the access request 1305 to a PCHR app 1355 resident on a registered patient device 1320. If the patient, from the PCHR app 1355, denies consent for access, the PCHR app 1355 may send an encrypted, digitally signed consent denied message 1360 to the PCHR record repository 1370, which decrypts the message and verifies a digital signature 1365.

If the patient has sent 1360 a denial of access message and, in spite of the message, the PCHR system determines that health claims payer 1302 has gained access to the patient record 1372, the PCHR system interprets such access as a breach 1390. In case of detection of such a breach, the PCHR system notifies 1310 the patient about the breach on the registered patient device 1320. In such a case, the PCHR 1370 also adds health claims payer 1302 to a list of users that are permanently denied 1330 access to the PCHR system such that health claims payer 1302 is not able to access any patient records in the future. Furthermore, the PCHR system also transfers 1340 administrator controls of the PCHR record repository 1370 to an independent security analyst 1350. The breach of the PCHR record repository 1370 may indicate that the administrator of the PCHR record repository 1370, either as a result of incompetence or bad intent, failed to ensure exclusive control of the patient over the patient record 1372. In such a case the PCHR system also provides the patient an option to delete all records from the PCHR record repository 1370 that was breached and to receive an encrypted copy of all contents of the patient record at a patient-designated storage location such as the patient registered device 1320.

Figure 14:
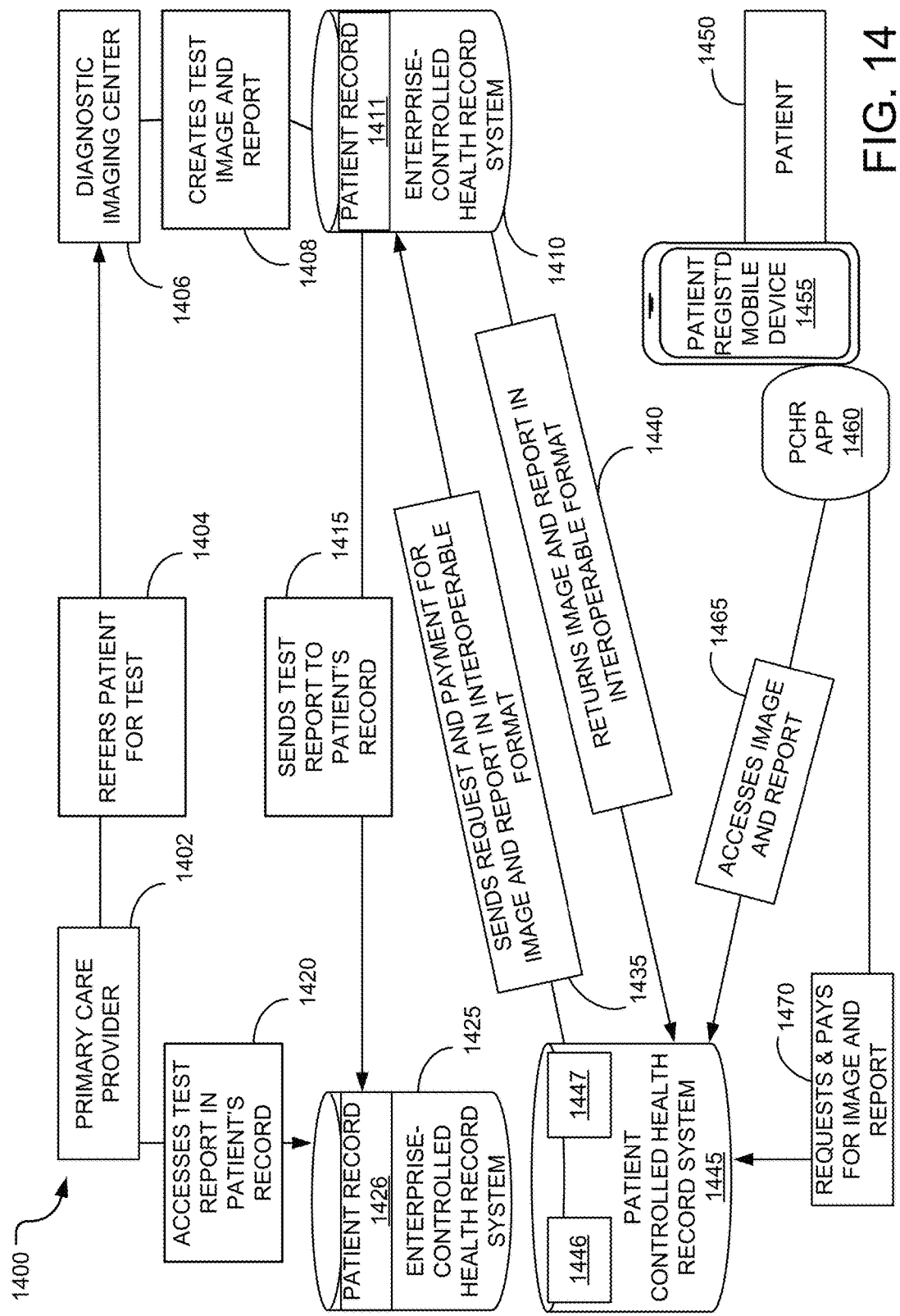
FIG. 14 is an example block diagram illustrating operations for the patient, from a registered device, to govern import of diagnostic images and reports from an enterprise-controlled electronic health record (ECHR) system into the patient record in the PCHR system.

FIG. 14 is an alternative example block diagram 1400 illustrating operations for obtaining and storing vital health information artifacts such as diagnostic images in PCHR patient records. Specifically the block diagram 1400 illustrates a process that prevents needless repetition of costly, uncomfortable and sometimes dangerous diagnostic tests as well as needless loss of baseline test results that may prove invaluable for future patient care. As an example, a primary care provider 1402 refers a patient 1450 for a diagnostic test 1404 at a diagnostic imaging center 1406. After the patient 1450 undergoes the diagnostic test 1404, the imaging center 1406 creates and stores a test image and report 1408 in the patient's record 1411 in the record repository of the imaging center's ECHR system 1410 and sends copies of the test image and report 1415 to a patient record 1426 in an ECHR system 1425 of primary care provider 1402. In this case, the primary care provider 1402 can directly access 1420 the test report from the patient record 1426.

In the illustrated implementation, the patient 1450, using a PCHR app 1460 resident on a registered patient device 1455 sends a request 1470 and pays for a copy of the test image and report 1408, which a PCHR system 1445 may send 1435 in an encrypted message to the imaging center's ECHR system 1410. Furthermore, the PCHR app 1460 may also access 1465 the image and the report from the PCHR system 1445. Because the PCHR system 1445 sends the message in industry-standard, encrypted, machine-readable format, the imaging center's ECHR system 1410, if interoperable, will be able to decrypt, parse, verify and process the request. The imaging center's ECHR system 1410 may return 1440 the test image and report 1408 to the PCHR system 1445, which authenticates the message sender and validates the integrity of message contents before tagging and storing the test image and report 1408 in a data hub 1447 of patient record 1446. In an alternative implementation, the ECHR system 1410 is either not interoperable or the imaging center's business policy requires the patient 1450 to appear in person and obtain the test image and report 1408 on a CD. After taking these steps, the patient 1450 may login to the PCHR system 1445 from a web-connected computer, consent to her own login from her registered device 1455, and upload the test report and image 1408 from a CD to the data hub 1447 of her patient record 1446.

Illustrated and alternative implementations of operations for obtaining and storing vital health information artifacts such as diagnostic images in PCHR patient records distinguish the PCHR system from an ECHR system. ECHR systems 1410, 1425 are designed and implemented for storage and retrieval of health information either created by the enterprise (the diagnostic imaging center 1406) or ordered by the enterprise (primary care provider 1402). Patient 1450 will get optimally safe and high quality care if primary care provider 1402 can evaluate not only test image and report 1408 but images and reports resulting from many comparable tests previously administered to patient 1450 that are now scattered, if still extant, in many inaccessible filing cabinets and ECHR systems. In contrast, the data hub of a PCHR patient record functions as a lifelong, healthcare enterprise neutral archive where patients and their various healthcare providers can rapidly find and utilize vital diagnostic images and other health information artifacts as required for coordinated, safe, high quality and efficient care.

Figure 15:
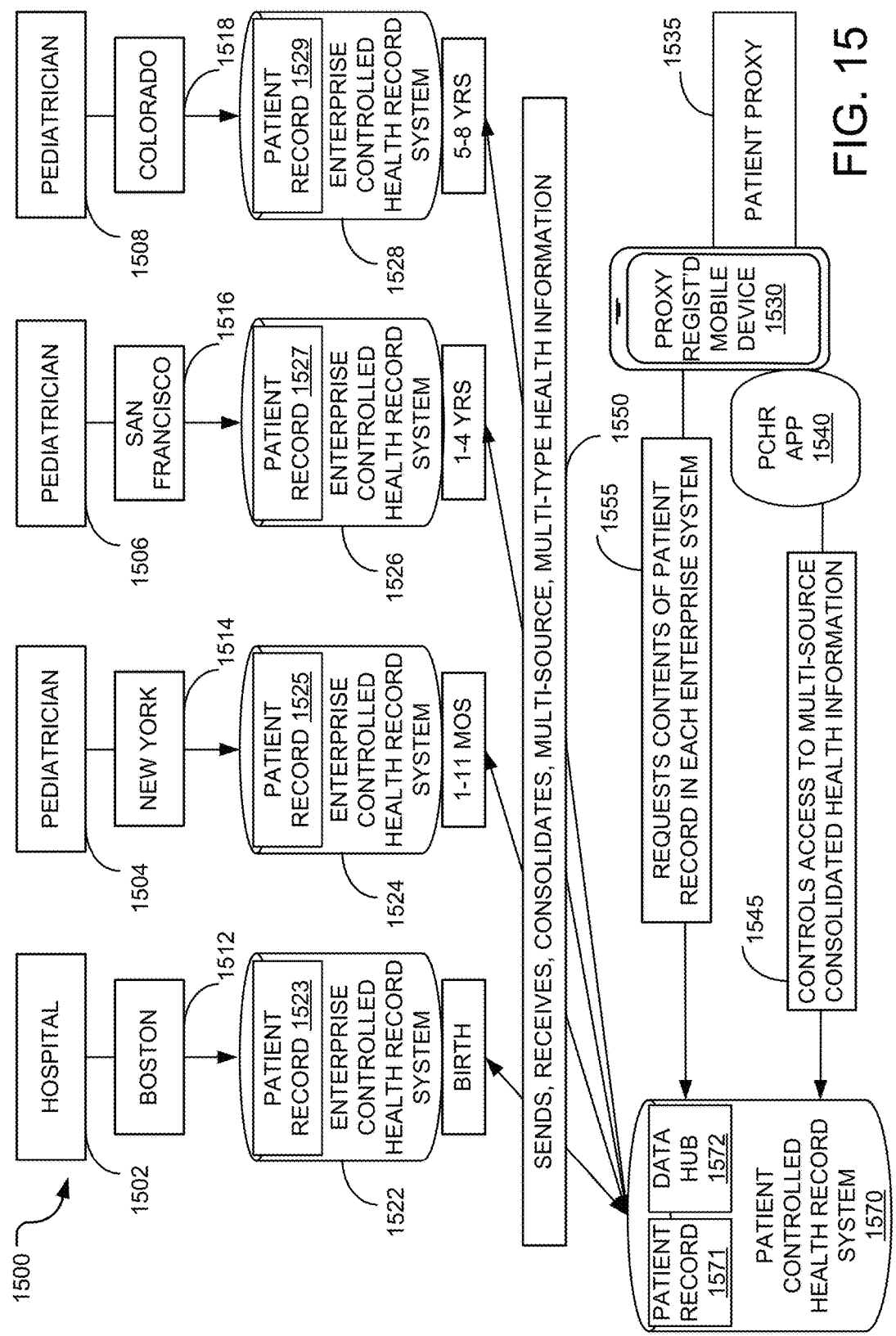
FIG. 15 is an example block diagram illustrating operations for the registered device of a patient proxy to govern import of artifacts, clinical summaries, and health insurance claims from multiple ECHR systems into the patient record in the PCHR system.

FIG. 15 is an example block diagram 1500 illustrating operations for integrating many types of health information obtained from many sources at many times into patient records in the PCHR system. The block diagram 1500 illustrates the ease with which a patient's health information, generated at a number of different locations over a long period of time, can be accessed with high efficiency and exclusive control using the PCHR system disclosed herein. For example, a patient may be born in a hospital 1502 in Boston 1512, resulting in the health information related to her birth being stored in a patient record 1523 of an ECHR system 1522. Subsequently, the patient, between the ages of 1 and 11 months, may be treated by a pediatrician 1504 in New York 1514, resulting in more health information being stored in patient record 1525 of an ECHR system 1524. Similarly, as the patient sees other pediatricians 1506 and 1508 in San Francisco 1516 and Colorado 1518, between the ages of 1 and 8 years, more health information is generated and stored in patient records 1527 and 1529 of ECHR systems 1526 and 1528. Thus, even before the patient is nine years old, she has fragments of health information stored in at least four ECHR system silos 1522-1528. Without great effort and expense, no future healthcare provider can obtain a comprehensive perspective on the patient's health history and status impeding efforts to diagnose and treat complex and rare childhood illnesses.

According to an implementation of the PCHR system disclosed herein, a patient proxy 1535, such as the patient's mother, uses a PCHR app 1540 resident on the registered patient proxy device 1530 to control 1545 and request 1555 through a PCHR system 1570 all contents of patient records 1523, 1525, 1527, 1529 in ECHR systems 1522, 1524, 1526, 1528. The patient's mother 1535 may submit these requests to the PCHR system 1570 all at once, each time the family moves to a new location, or when the child is fifteen and undergoing an extensive diagnostic evaluation. Because the PCHR system 1570 sends the messages in industry-standard, encrypted, machine-readable format, ECHR systems 1522, 1524, 1526, 1528, if interoperable, will be able to decrypt, parse, verify and process the requests. The ECHR systems 1522, 1524, 1526, 1528 may return 1550 contents of patient records 1523, 1525, 1527, 1529 in industry-standard, encrypted, machine-readable messages to the PCHR system 1570, which authenticates message senders and validates the integrity of message contents before storing the enclosed health information in a data hub 1572 of a patient record 1571. When ECHR systems 1522, 1524, 1526, 1528 return the requested health information, the PCHR system authenticates message senders and validates the integrity of message contents before tagging, consolidating, and storing requested health information in the patient record of the PCHR record repository 1570.

In an alternative implementation, ECHR systems 1522, 1524, 1526, 1528 are either not interoperable or their business policies require patient proxy 1535 to appear in person and obtain record contents on a CD. After taking these steps, patient proxy 1535 may login to the PCHR system 1570 from a web-connected computer, consent to her own login from her registered device 1530, and upload the contents of patient records 1523, 1525, 1527, 1529 from CDs to the data hub 1572 of patient record 1571. Patient proxy 1535 may show the data hub timeline on her device to future healthcare providers, who touch links and swipe through screens for a quick scan of patient history and status. Subsequently, patient proxy 1535 may use her device to authorize providers to access, download and study selected data hub contents from their web-connected computers.

Illustrated and alternative implementations of operations for integrating many types of health information obtained from many sources at many times into patient records in the PCHR system distinguish the PCHR system 1570 from ECHR systems 1522, 1524, 1526, 1528, which capture and store health information related to the services the healthcare enterprises supply during one time period in the patient's life. Patients move frequently from one healthcare provider to another due to provider availability, health insurance coverage, changes in residence, etc. Patients with chronic illnesses are treated by as many as twelve different providers at one time. Healthcare providers usually supplement the limited information in their ECHR systems by interviewing patients and relatives, who admittedly give inaccurate, incomplete responses due to anxiety, faulty memory and incomprehension. The PCHR system supports patients in their efforts to inform providers about their health history and status. A patient proxy can hand a provider her mobile device and let him see and explore the data hub timeline of a patient's PCHR record with its links to tamper-proof health information artifacts from trustworthy sources.

Figure 16:
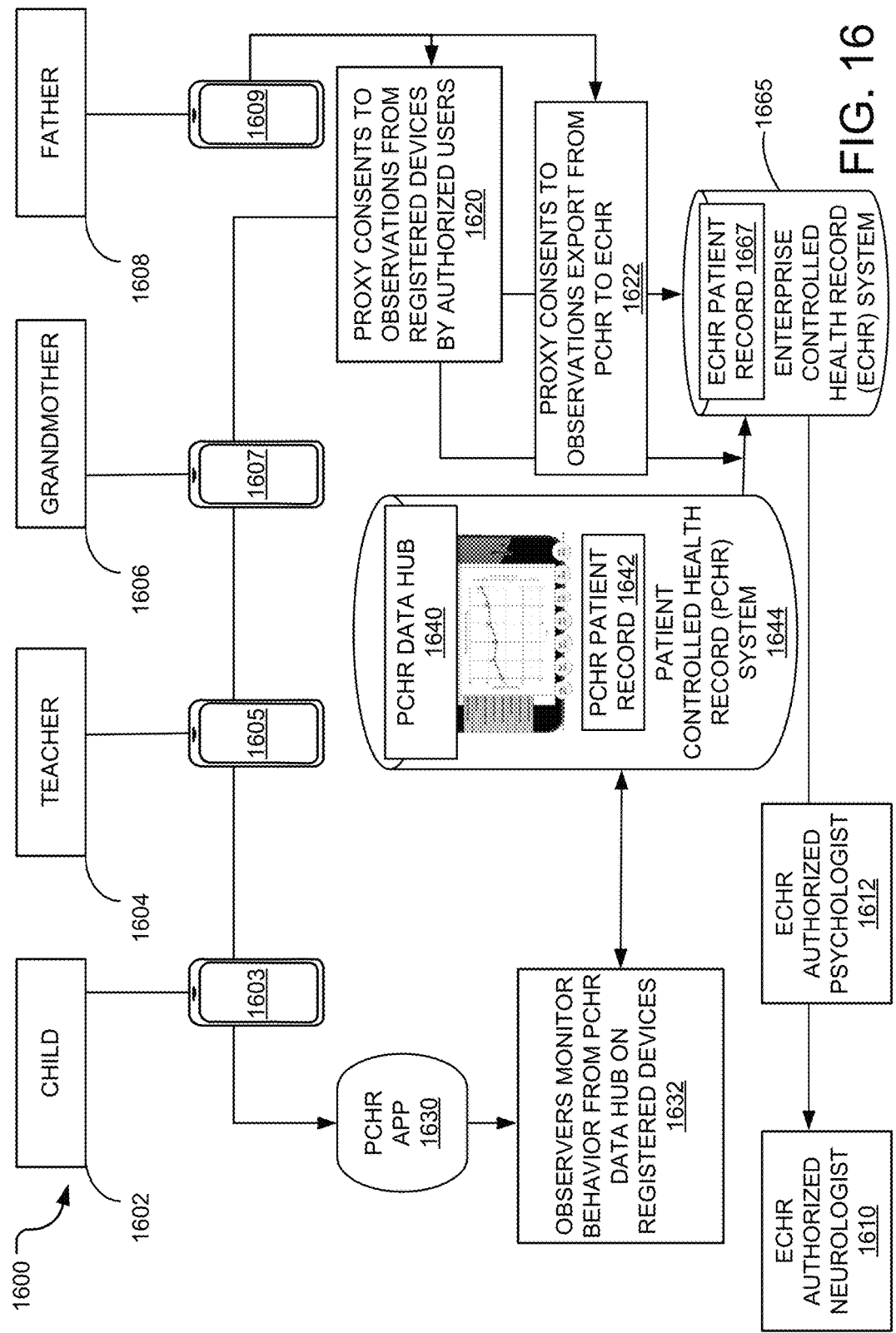
FIG. 16 is an example block diagram illustrating operations for a patient and patient proxies, from their registered devices, to enter independent observations into the patient record in the PCHR system and to simultaneously view an integrated display of the totality of observations.

FIG. 16 is an example block diagram 1600 illustrating operations for patient-controlled collection, display, analysis, storage, and sharing of behavioral observations by several concurrent observers. In the illustrated implementation 1600, a child patient 1602 with epilepsy exhibits frequent emotional outbursts, a likely side effect of anti-convulsant medication prescribed by the child's pediatric neurologist 1610. At the advice of a psychologist 1612, the child's father 1608 uses his registered mobile device 1609 to consent 1620 to the monitoring of emotional outbursts by himself, the child 1602, the child's teacher 1604, and the child's grandmother 1606 on their registered mobile devices 1603, 1605, 1607 and to visualization of their collective observations on the PCHR data hub 1640 of their registered devices. Furthermore, the child's father 1608 uses his registered mobile device 1609 to consent to 1622 export of observations from the patient record 1642 in PCHR system 1644 to patient record 1667 in ECHR system 1665, where observations are available to the neurologist 1610 and the psychologist 1612 who are authorized ECHR users.

In another implementation, the neurologist 1610 may evaluate the impact of a different dosage of anti-convulsant medication by referring to the continuing observations of the child 1602, the child's teacher 1604, grandmother 1606 and father 1608. In an additional example implementation, the neurologist 1610 may engage the child 1602, the child's teacher 1604, grandmother 1606 and father 1608 in monitoring both compliance with administration of anti-convulsant medication and emotional outbursts. In yet another implementation, the psychologist 1612 may engage the child 1602, the child's teacher 1604, grandmother 1606 and father 1608 in using their registered devices 1603 1605 1607 1609 to monitor compliance and emotional outbursts and reward the child for medication compliance and self-control.

In an alternative example implementation, the child 1602 has been diagnosed with epilepsy and type 1 diabetes. The neurologist 1610 and the psychologist 1612 question the contributions of anti-convulsant medication and glycemic control alone and together to emotional outbursts. Therefore, the father 1608 equips the child 1602 with a wristband blood glucose meter that communicates from a PCHR app 1630 resident on the child's registered device 1603 with the PCHR data hub 1640, which merges glucose meter results with behavioral observations of the child 1602, the child's teacher 1604, grandmother 1606 and father 1608. The father 1608 consents 1622 to export of the merged observations from the child's record 1642 in the PCHR system 1644 to the child's record 1667 in the ECHR system 1665 for availability to the neurologist 1610 and the psychologist 1620, who may, based on merged observations, recommend initial changes in the child's exercise regimen rather than in medication dosage.

Illustrated and alternative implementations of operations for patient-controlled collection, display, analysis, storage, and sharing of behavioral observations distinguish a PCHR system 1644 from an ECHR system 1665, which is designed for storage and retrieval of standardized health information collected by healthcare professionals who work for the healthcare enterprise, not for idiosyncratic observations of patient behavior. Yet, healthcare professionals have long relied on the behavioral observations of patients, parents, and teachers for diagnostic and treatment planning purposes and are increasingly recommending that patients use health apps on their mobile devices to collect behavioral observations and to monitor 1632 physiological parameters such as blood glucose, activity, heart rate and blood pressure. A PCHR system enables patients and their support teams to collect, visualize and share merged behavioral observations and physiological results as the basis for day to day practical decisions about healthcare self-management and as the basis for evidence-based shared decision making with healthcare providers who can access patient-collected observations and results from their ECHR systems.

Figure 17:
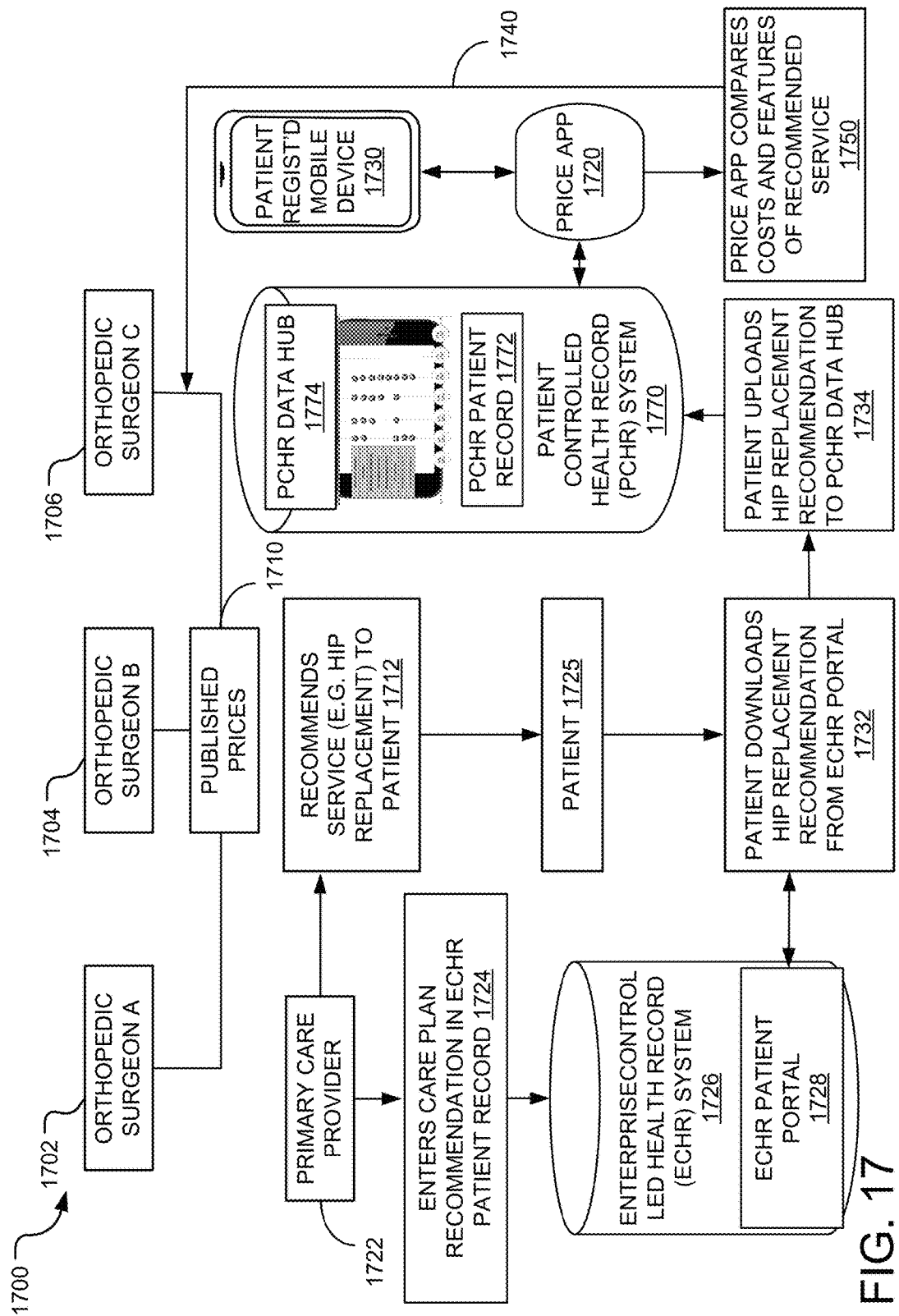
FIG. 17 is an example block diagram illustrating operations for a patient, from a registered device, to govern comparison-shopping for provider-recommended services and products documented in the patient record in the PCHR system.

FIG. 17 is an example block diagram 1700 illustrating operations in a market for provider-recommended services and products in the patient controlled health record (PCHR) system disclosed herein. A primary care provider 1722 may recommend a costly service 1712, such as hip replacement, to a patient 1725, entering the care plan detailing this recommendation into a patient record 1724 of an enterprise controlled health record (ECHR) system 1726. The patient 1725 downloads the care plan detailing a hip replacement recommendation 1732 from an ECHR system patient portal 1728 and uploads a care plan 1734 to a PCHR data hub 1774. In such a case, the patient 1725 uses a price app 1720 resident on a patient registered mobile device 1730. The price app 1720 is able to access the care plan detailing the hip replacement recommendation from the PCHR data hub 1774 and using such information, the price app 1720, without disclosing sensitive and personally identifiable patient health information, searches for 1740 information comparing the costs and features of recommended services in the patient's preferred geographical region and health insurance network 1750, such as published prices 1710 of orthopedic surgeons 1702, 1704, 1706, and reports the results to the PCHR data hub 1774.

Based on the report from the price app 1720, this implementation may further allow (not shown) the patient 1725 to select one of the orthopedic surgeons 1702-1706, communicate this choice to primary care provider 1722 via the ECHR patient portal 1728 and request that the primary care provider 1722 refer the patient 1725 to the selected surgeon for follow through with the recommended care plan. In an alternative implementation, the price app 1720, without disclosing sensitive and personally identifiable patient health information, searches for 1740 the best price for a costly drug prescribed for the patient 1725 by primary care provider 1722 and reports the results to the PCHR data hub 1774. In yet another implementation, after finding the best price for the prescribed drug, the patient 1725 and primary care provider 1722 may jointly employ the concurrent observations management module disclosed herein to evaluate the impact of the drug on patient health outcomes.

Illustrated 1700 and alternative implementations of operations for private comparison shopping for recommended healthcare products and services distinguish an ECHR system 1726, which is designed for healthcare providers to store and retrieve patient care plan recommendations, from a PCHR system 1770, which is designed for patients to store PCHR patient records 1772 and to adhere to providers' care plan recommendations in the most cost-effective manner possible, but without exposing sensitive health information during public searches of the internet.

Figure 18:
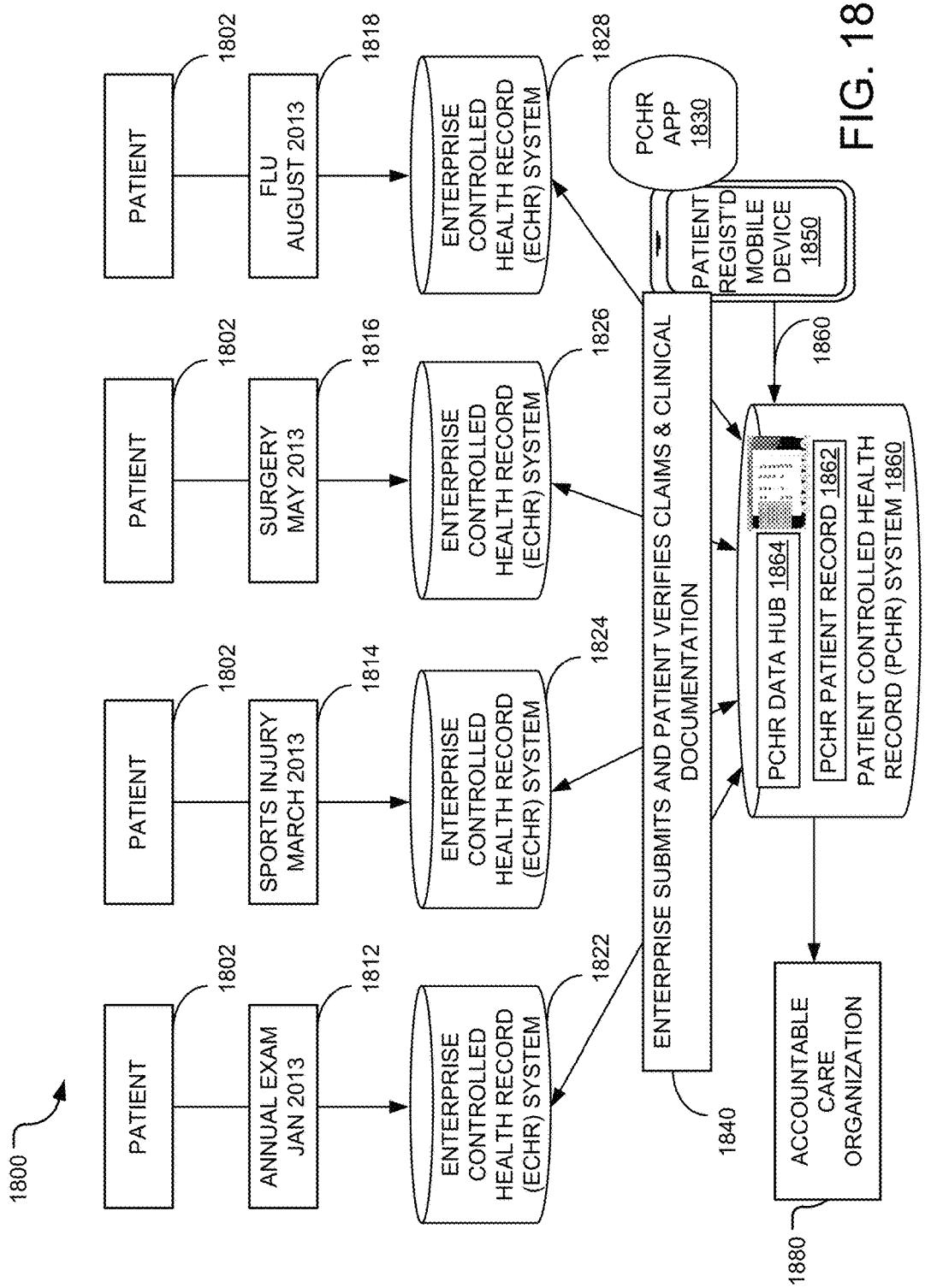
FIG. 18 is an example block diagram illustrating operations for a patient, from a registered device, to govern verification of claims submitted by healthcare enterprises to health insurance payers documented in the patient record in the PCHR.

FIG. 18 is an example block diagram 1800 illustrating operations allowing for a patient 1802 to verify 1840 the accuracy of claims and clinical documentation submitted by healthcare providers for services 1812-1818 rendered to patient 1802 and billed to a third-party payer such as an accountable care organization 1880. For example, an accountable care organization 1880 may award incentives to healthcare providers whose ECHR systems 1822-1828 submit claims and clinical documentation related to an annual exam 1812, a sports injury 1814, a surgery 1816, and flu 1818 through a PCHR system 1860. Subsequently, the PCHR system 1860 consolidates information in the PCHR patient record about provider services and provider billing for those services and displays the consolidated information to the patient 1802 through a PCHR data hub 1864. The patient 1802, from a PCHR app 1830 resident on a registered mobile device 1850 may communicate privately with the accountable care organization 1880 about questionable and erroneous claims and documentation such as an invoice for a physical the provider cancelled. The PCHR system 1860 also stores enterprise submitted claims and clinical documentation 1840 in PCHR patient record 1862.

In an alternative implementation, a self-insured employer bundles a PCHR patient record with its employee benefits plan, so that an employee 1802 from the PCHR app 1830 resident on his registered mobile device 1850 may communicate privately with the plan administrator about questionable and erroneous claims and clinical documentation.

Illustrated 1800 and alternative implementations of operations for patient verification of claims and clinical documentation distinguish an ECHR system 1826, which enables healthcare providers to document and bill for their services, from a PCHR system 1860, which matches information about services rendered with bills and documentation and enables patients to identify and dispute claims for unsatisfactory and improperly billed products and services.

Figure 19:
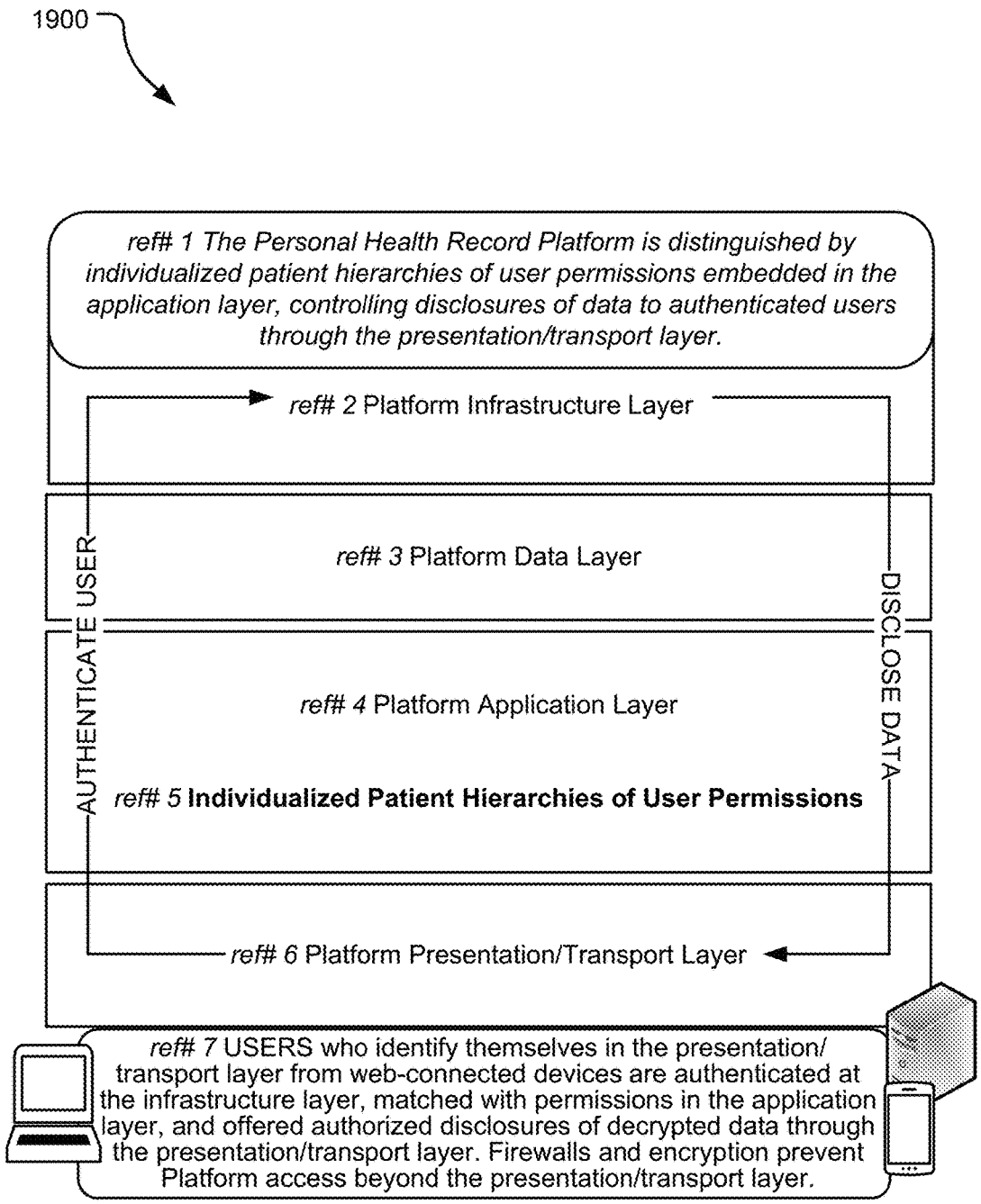
FIG. 19 illustrates an n-tier architecture of the PCHR system disclosed herein, in which individualized patient hierarchies of user permissions regulate authentication of users who attempt entry to patient records and disclosure of data to users after successful authentication.

FIG. 19 illustrates an n-tier architecture 1900 of the PCHR system disclosed herein, in which individualized patient hierarchies of user permissions regulate authentication of users who attempt entry to patient records and disclosure of data to users after successful authentication. Specifically, the implementation disclosed in FIG. 19 illustrates that the PCHR system comprises four separately encrypted, firewall protected layers that interact with each other, giving rise to the System's capabilities, distinguished by individualized patient hierarchies of user permissions embedded in the application layer, controlling disclosures of data to authenticated users through the presentation/transport layer (ref#1). An infrastructure layer (ref#2), defined as offering the basic structures needed for System operation, includes components such as programming logic, relational databases, authentication and cryptography. A data layer, defined as offering the application layer access to data stored in the infrastructure layer, includes data segments such as conditions, medications, allergies, procedures, recommendations and observations (ref#3). An application layer, defined as offering business rules needed for communications within and between layers, includes embedded patient user permission hierarchies, public policies and evidence-based clinical and practice guidelines (ref#4). And, a presentation/transport layer, defined as offering delivery and formatting of information to the application layer for further processing or display and decryption of data presented or transported to users, includes user interfaces for patients, providers without EHRs, administrators, researchers, health information exchanges and health insurance payers; web services, defined as a method of communication between two electronic devices over the web; and, tools for data exchange between patient PCHRs and provider EHRs (ref#6).

In particular, FIG. 19 shows that the PCHR system is distinguished from conventional EHRs by individualized patient hierarchies of user permissions embedded in the application layer (ref#5), controlling disclosures of data to authenticated users through the presentation/transport layer in the following way. Users who identify themselves in the presentation/transport layer from web-connected devices are authenticated at the infrastructure layer, matched with permissions in the application layer, and offered authorized disclosures of decrypted data through the presentation/layer. Firewalls and encryption prevent Program access by any user beyond the presentation/transport layer (ref#7).

Figure 20:
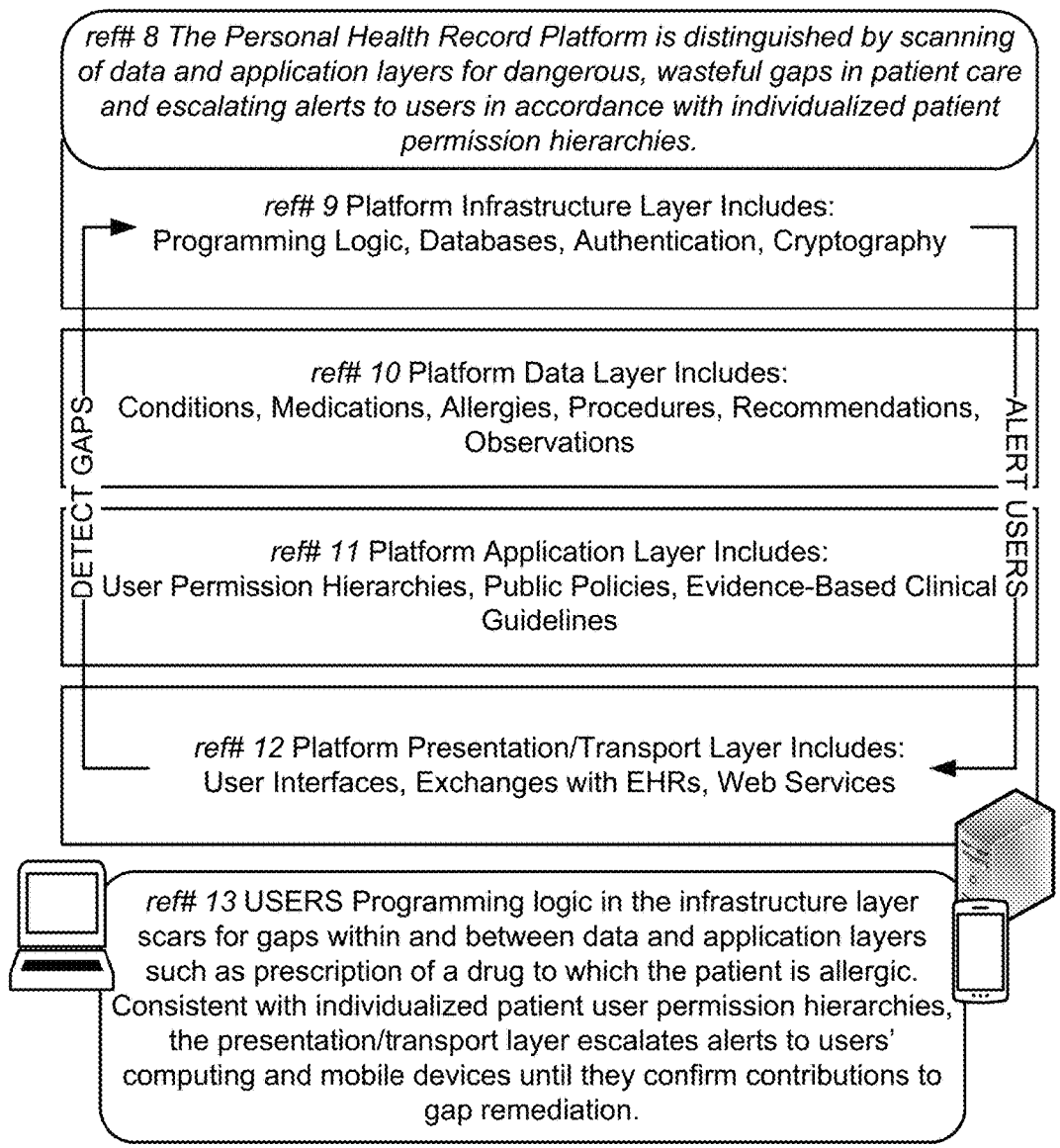
FIG. 20 illustrates that the example PCHR system disclosed herein is distinguished by scanning of data and application layers for gaps in patient care and escalating alerts to users with suitable permissions through the presentation/transport layer.

FIG. 20 illustrates that the example PCHR system disclosed herein is distinguished by scanning of data and application layers for gaps in patient care and escalating alerts to users with suitable permissions through the presentation/transport layer. Specifically, FIG. 20 illustrates components of the infrastructure layer of the PCHR system disclosed herein. Specifically, the components of the PCHR system infrastructure layer (programming logic, databases, authentication, and cryptography) (ref#9), of the data layer (conditions, medications, allergies, procedures, recommendations, and observations) (ref#10), of the application layer (user permission hierarchies, public policies, evidence-based clinical guidelines) (ref#11), and of the presentation/transport layer (user interfaces, tools for automating exchange of data in PCHRs with electronic health records (EHRs), and webs services) (ref#12) related to detection of gaps in patient care, illustrating that interactions between System layers and within the components of each layer give rise to capabilities for detection of gaps in patient care and alerting of users. In particular, FIG. 20 shows that the PCHR system is distinguished by scanning of data and application layers for gaps in patient care and escalating alerts to users with suitable permissions (ref#8). Programming logic in the infrastructure layer (ref#9) scans for gaps within and between data and application layers (ref#10, 11) such as prescription of a drug to which the patient is allergic or a diagnostic test that has been recommended but not completed. Consistent with individualized hierarchies of permissions, the presentation/transport layer (ref#13) sends and escalates alerts to users' computing devices, including mobile devices, indicating that a contraindicated drug has been prescribed, until the primary provider confirms the gap has been addressed (e.g., patient told to discontinue contraindicated drug) (ref#13).

Figure 21:
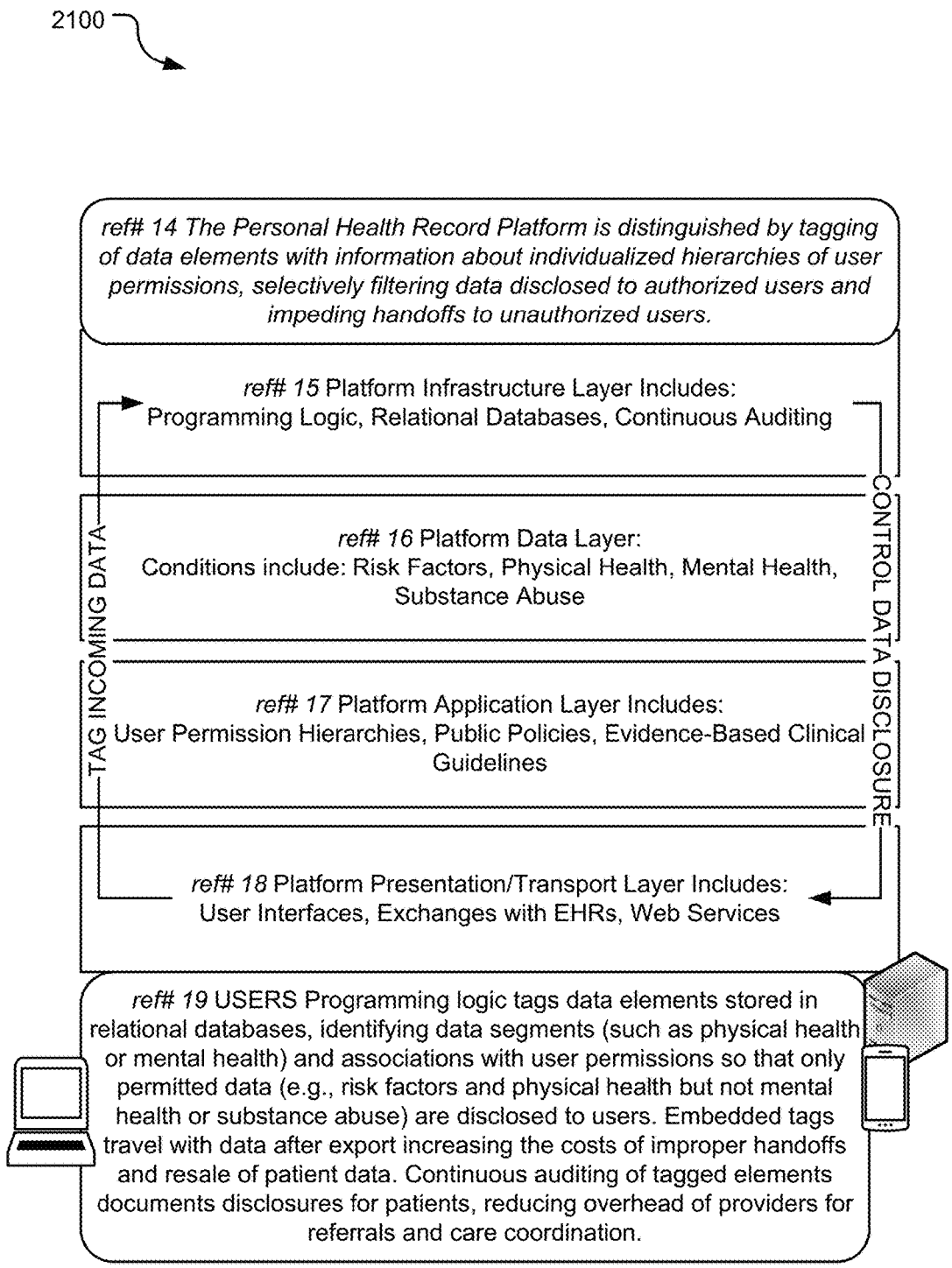
FIG. 21 illustrates that the example PCHR system disclosed herein is distinguished by tagging of data elements stored in relational databases with information about individualized hierarchies of user permissions, selective filtering data disclosed to authorized users through the presentation/transport layer and impeding handoffs to unauthorized users.

FIG. 21 illustrates that the example PCHR system disclosed herein is distinguished by tagging of data elements stored in relational databases with information about individualized hierarchies of user permissions, selective filtering of data disclosed to authorized users through the presentation/transport layer and impeding of handoffs to unauthorized users. Specifically, FIG. 21 illustrates components of the PCHR system infrastructure layer (programming logic, relational databases, continuous auditing) (ref#15), of the data layer (risk factors, physical health, mental health and substance abuse conditions) (ref#16), of the application layer (user permission hierarchies, public policies, evidence-based clinical guidelines) (ref#17), and of the presentation/transport layer (user interfaces, tools for data exchange between patient PCHRs and provider electronic health records (EHRs), and web services) (ref#18) related to tagging of data elements with information about individualized hierarchies of user permissions, illustrating that interactions between System layers and within the components of each layer give rise to capabilities for tagging incoming data and controlling data disclosures. In particular, FIG. 21 shows that the PCHR system is distinguished by tagging of data elements (defined as the smallest meaningful units of data) with information about individualized hierarchies of user permissions, selectively filtering data disclosures to authorized users and impeding handoffs of data to unauthorized users (ref#14) via the presentation/transport layer. Programming logic tags data elements stored in relational databases, identifying data segments (such as physical health or mental health) and associations with user permissions so that only permitted data (e.g., risk factors and physical health but not mental health or substance abuse) are disclosed to users. Embedded tags travel with data after export increasing the costs of improper handoffs and resale of patient data. Based on continuous auditing of tagged elements, reports are available to patients about disclosures of their data, so that providers need not manually document such disclosures during referrals and care coordination (ref #19).

Figure 22:
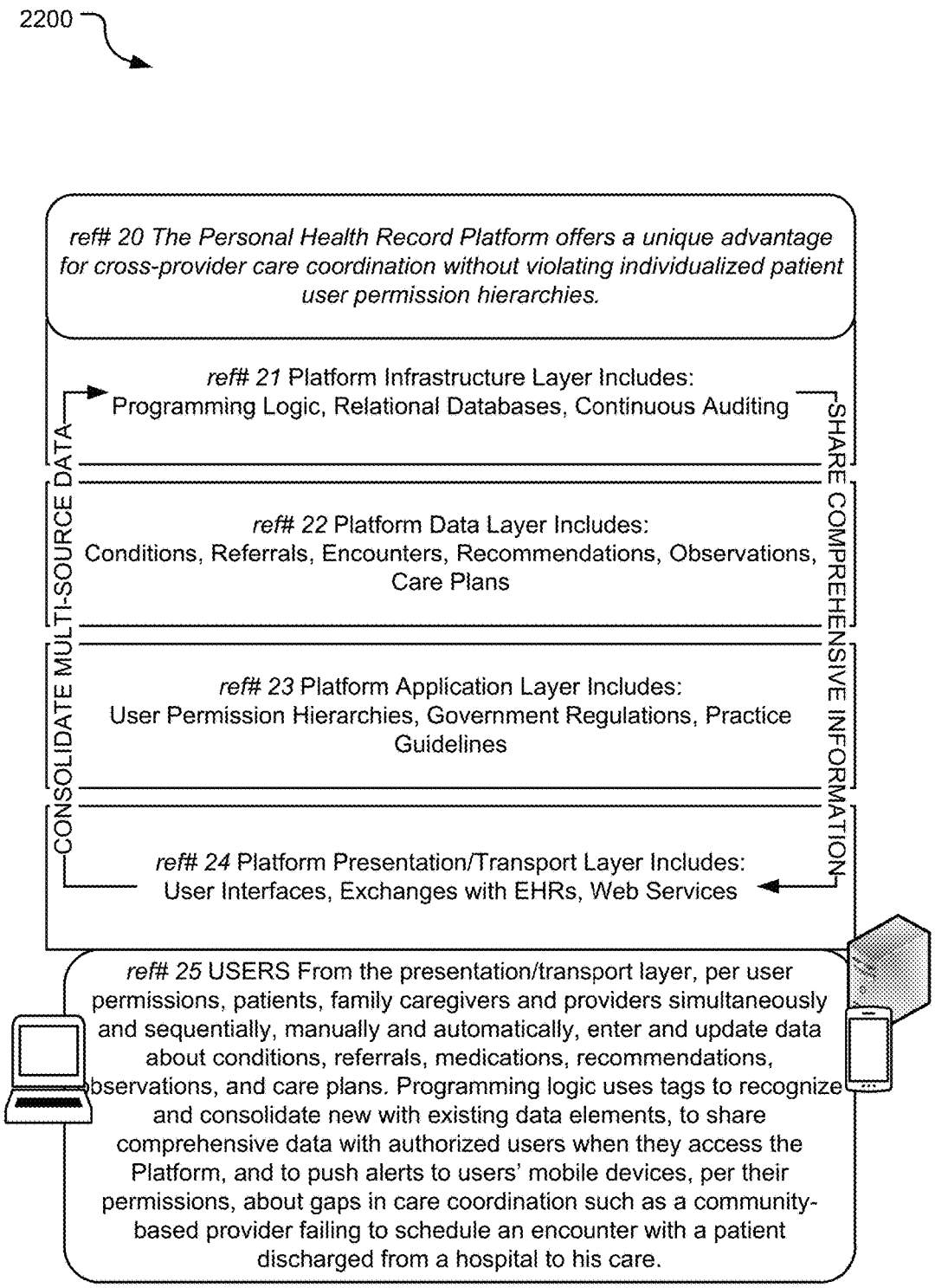
FIG. 22 illustrates the advantage, for cross-provider care coordination without violation of individualized patient permission hierarchies, offered by the example PCHR system disclosed herein.

FIG. 22 illustrates the advantage, for cross-provider care coordination without violation of individualized patient permission hierarchies, offered by the example PCHR system disclosed herein. Specifically, FIG. 22 illustrates components of the PCHR system infrastructure layer (programming logic, relational databases, continuous auditing) (ref#21), of the data layer (conditions, referrals, encounters, recommendations, observations, care plans) (ref#22), of the application layer (user permission hierarchies, government regulations, practices guidelines) (ref#23), and of the presentation/transport layer (user interfaces, tools for data exchange between patient PCHRs and provider electronic health records (ECHRs), and web services) (ref#24) related to cross-provider care coordination without violation of individualized patient hierarchies of user permissions and illustrating that interactions between System layers and within the components of each layer give rise to capabilities for consolidating multi-source incoming data and sharing comprehensive outgoing data.

In particular, FIG. 22 shows that the PCHR system offers an advantage, compared to conventional ECHRs and patient portals tethered to ECHRs, for cross-provider care coordination without violation of a patient's individualized user permission hierarchies (ref#20). From the presentation/transport layer (ref#24), per user permissions (ref#23), patients, family caregivers and providers simultaneously and sequentially, manually and automatically, enter and update data about conditions, referrals, medications, recommendations, observations, and care plans (ref#22). Programming logic (ref#21) uses tags to recognize and consolidate new with existing data elements, to share comprehensive data with authorized users when they access the system, and to push alerts to users' computing devices, including mobile devices, per patient authorized permissions, about gaps in care such as a community-based provider failing to schedule an encounter with a patient discharged from a hospital to the provider's care (ref#25).

Figure 23:
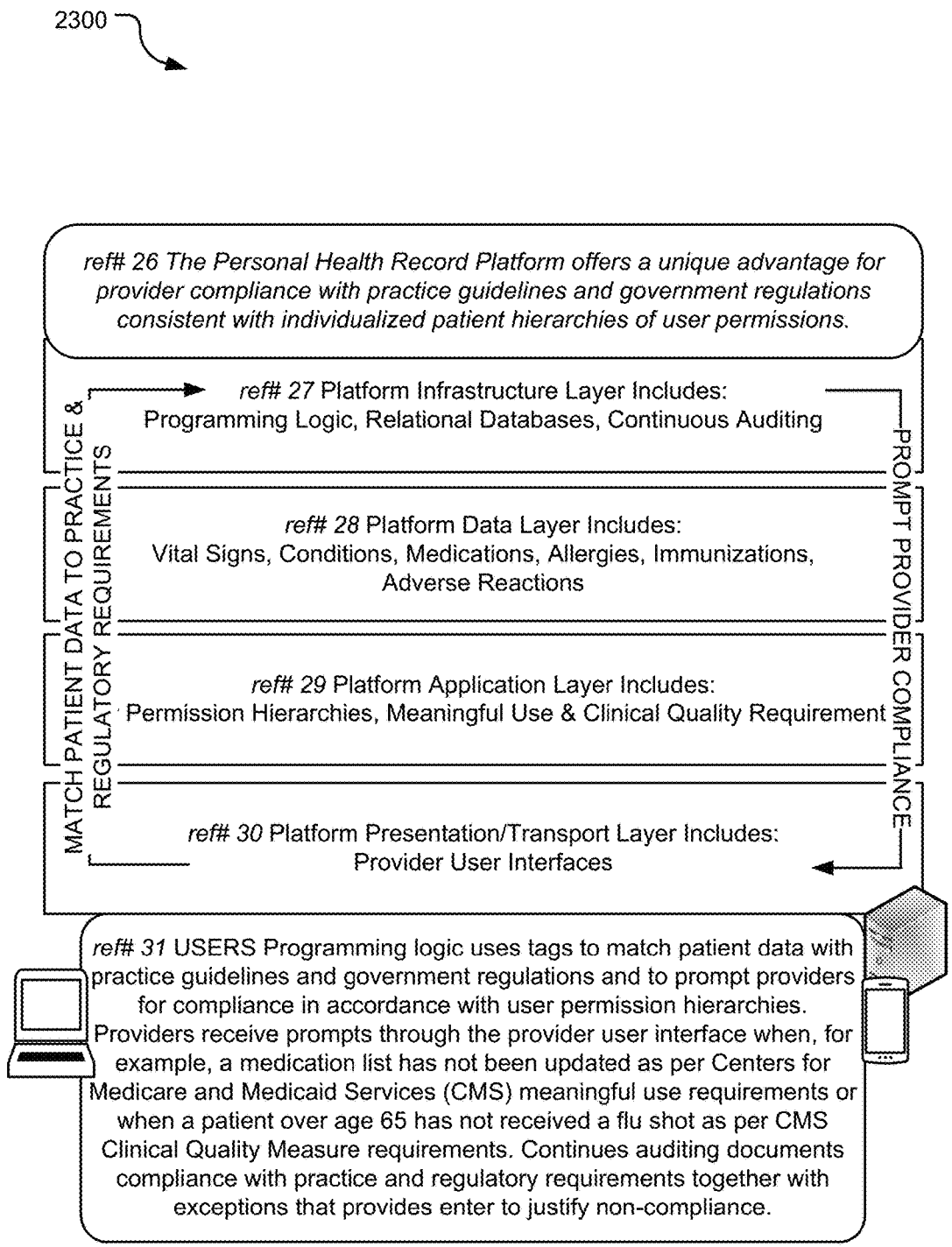
FIG. 23 illustrates the advantage, for provider compliance with practice guidelines and government regulations consistent with individualized patient permission hierarchies, offered by the example PCHR system disclosed herein.

FIG. 23 illustrates the advantage, for provider compliance with practice guidelines and government regulations, consistent with individualized patient permission hierarchies, offered by the example PCHR system disclosed herein. Specifically, FIG. 23 illustrates components of the infrastructure layer (programming logic, relational databases, continuous auditing) (ref#27), of the data layer (vital signs, conditions, medications, allergies, immunizations, adverse reactions) (ref#28), of the application layer (user permission hierarchies, meaningful use and clinical quality measure requirements) (ref#29), and of the presentation/transport layer (user interfaces, tools for data exchange between patient PCHRs and provider electronic health records (EHRs), and web services) (ref#30) related to provider compliance with practice guidelines and government regulations without violation of individualized patient hierarchies of user permissions, and illustrating that interactions between System layers and within the components of each layer give rise to capabilities for matching incoming patient data to practice regulatory requirements and sending outgoing prompts to providers about compliance.

Figure 24:
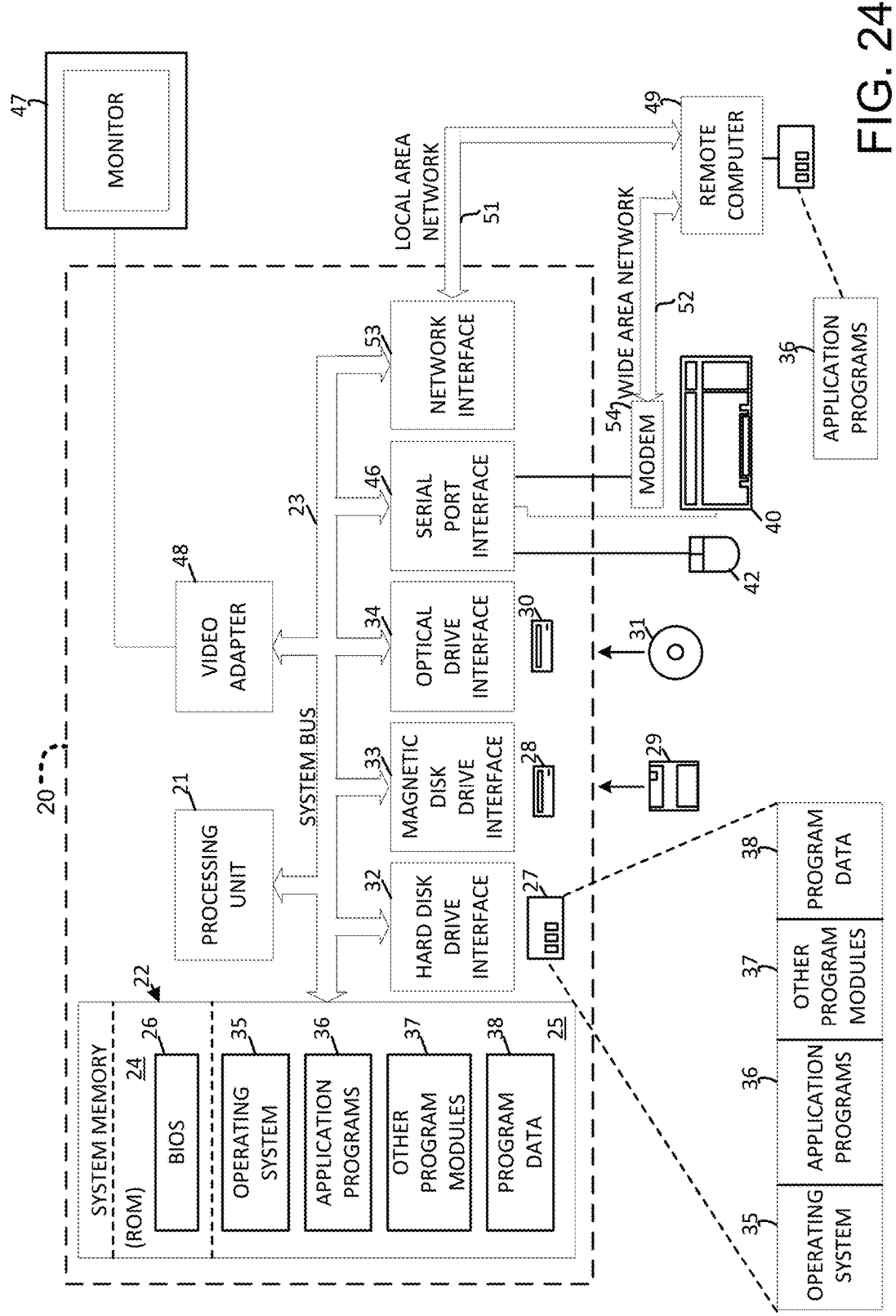
FIG. 24 illustrates an example computing system that may be used to implement the PCHR system disclosed herein.

In particular, FIG. 23 shows that PCHR system offers a unique advantage for provider compliance with practice guidelines and government regulations without violation of individualized patient hierarchies of user permissions (ref#26). Programming logic uses tags to match patient data with practice guidelines and government regulations and to prompt providers for compliance in accordance with user permission hierarchies. Providers receive prompts through the provider user interface (ref#30) when, for example, a medication list has not been updated as per Centers for Medicare and Medicaid Services (CMS) meaningful use requirements or when a patient over age 65 has not received a flu shot as per CMS Clinical Quality Measure requirements. Continuous auditing documents compliance with practice guidelines and regulations together with exceptions that providers enter to justify non-compliance FIG. 24 illustrates an example system that may be useful in implementing the described technology. The example hardware and operating environment of FIG. 24 for implementing the described technology includes a computing device, such as general purpose computing device in the form of a gaming console or computer 20, a mobile telephone, a personal data assistant (PDA), a set top box, or other type of computing device. In the implementation of FIG. 24, for example, the computer 20 includes a processing unit 21, a system memory 22, and a system bus 23 that operatively couples various system components including the system memory to the processing unit 21. There may be only one or there may be more than one processing unit 21, such that the processor of computer 20 comprises a single central-processing unit (CPU), or a plurality of processing units, commonly referred to as a parallel processing environment. The computer 20 may be a conventional computer, a distributed computer, or any other type of computer; the implementations are not so limited.

The system bus 23 may be any of several types of bus structures including a memory bus or memory controller, a peripheral bus, a switched fabric, point-to-point connections, and a local bus using any of a variety of bus architectures. The system memory may also be referred to as simply the memory, and includes read only memory (ROM) 24 and random access memory (RAM) 25. A basic input/output system (BIOS) 26, containing the basic routines that help to transfer information between elements within the computer 20, such as during start-up, is stored in ROM 24. The computer 20 further includes a hard disk drive 27 for reading from and writing to a hard disk, not shown, a magnetic disk drive 28 for reading from or writing to a removable magnetic disk 29, and an optical disk drive 30 for reading from or writing to a removable optical disk 31 such as a CD ROM, DVD, or other optical media.

The hard disk drive 27, magnetic disk drive 28, and optical disk drive 30 are connected to the system bus 23 by a hard disk drive interface 32, a magnetic disk drive interface 33, and an optical disk drive interface 34, respectively. The drives and their associated tangible computer-readable media provide nonvolatile storage of computer-readable instructions, data structures, program modules and other data for the computer 20. It should be appreciated by those skilled in the art that any type of tangible computer-readable media which can store data that is accessible by a computer, such as magnetic cassettes, flash memory cards, digital video disks, random access memories (RAMs), read only memories (ROMs), and the like, may be used in the example operating environment.

A number of program modules may be stored on the hard disk, magnetic disk 29, optical disk 31, ROM 24, or RAM 25, including an operating system 35, one or more application programs 36, other program modules 37, and program data 38. A user may enter commands and information into the personal computer 20 through input devices such as a keyboard 40 and pointing device 42. Other input devices (not shown) may include a microphone (e.g., for voice input), a camera (e.g., for a natural user interface (NUI)), a joystick, a game pad, a satellite dish, a scanner, or the like. These and other input devices are often connected to the processing unit 21 through a serial port interface 46 that is coupled to the system bus, but may be connected by other interfaces, such as a parallel port, game port, or a universal serial bus (USB). A monitor 47 or other type of display device is also connected to the system bus 23 via an interface, such as a video adapter 48. In addition to the monitor, computers typically include other peripheral output devices (not shown), such as speakers and printers.

The computer 20 may operate in a networked environment using logical connections to one or more remote computers, such as remote computer 49. These logical connections are achieved by a communication device coupled to or a part of the computer 20; the implementations are not limited to a particular type of communications device. The remote computer 49 may be another computer, a server, a router, a network PC, a client, a peer device or other common network node, and typically includes many or all of the elements described above relative to the computer 20, although only a memory storage device 50 has been illustrated in FIG. 24. The logical connections depicted in FIG. 24 include a local-area network (LAN) 51 and a wide-area network (WAN) 52. Such networking environments are commonplace in office networks, enterprise-wide computer networks, intranets and the Internet, which are all types of networks.

When used in a LAN-networking environment, the computer 20 is connected to the local network 51 through a network interface or adapter 53, which is one type of communications device. When used in a WAN-networking environment, the computer 20 typically includes a modem 54, a network adapter, a type of communications device, or any other type of communications device for establishing communications over the wide area network 52. The modem 54, which may be internal or external, is connected to the system bus 23 via the serial port interface 46. In a networked environment, program engines depicted relative to the personal computer 20, or portions thereof, may be stored in the remote memory storage device. It is appreciated that the network connections shown are example and other means of and communications devices for establishing a communications link between the computers may be used.

In an example implementation, software or firmware instructions and data for providing a search management system, various applications, search context pipelines, search services, service, a local file index, a local or remote application content index, a provider API, a contextual application launcher, and other instructions and data may be stored in memory 22 and/or storage devices 29 or 31 and processed by the processing unit 21.

Figure 25:
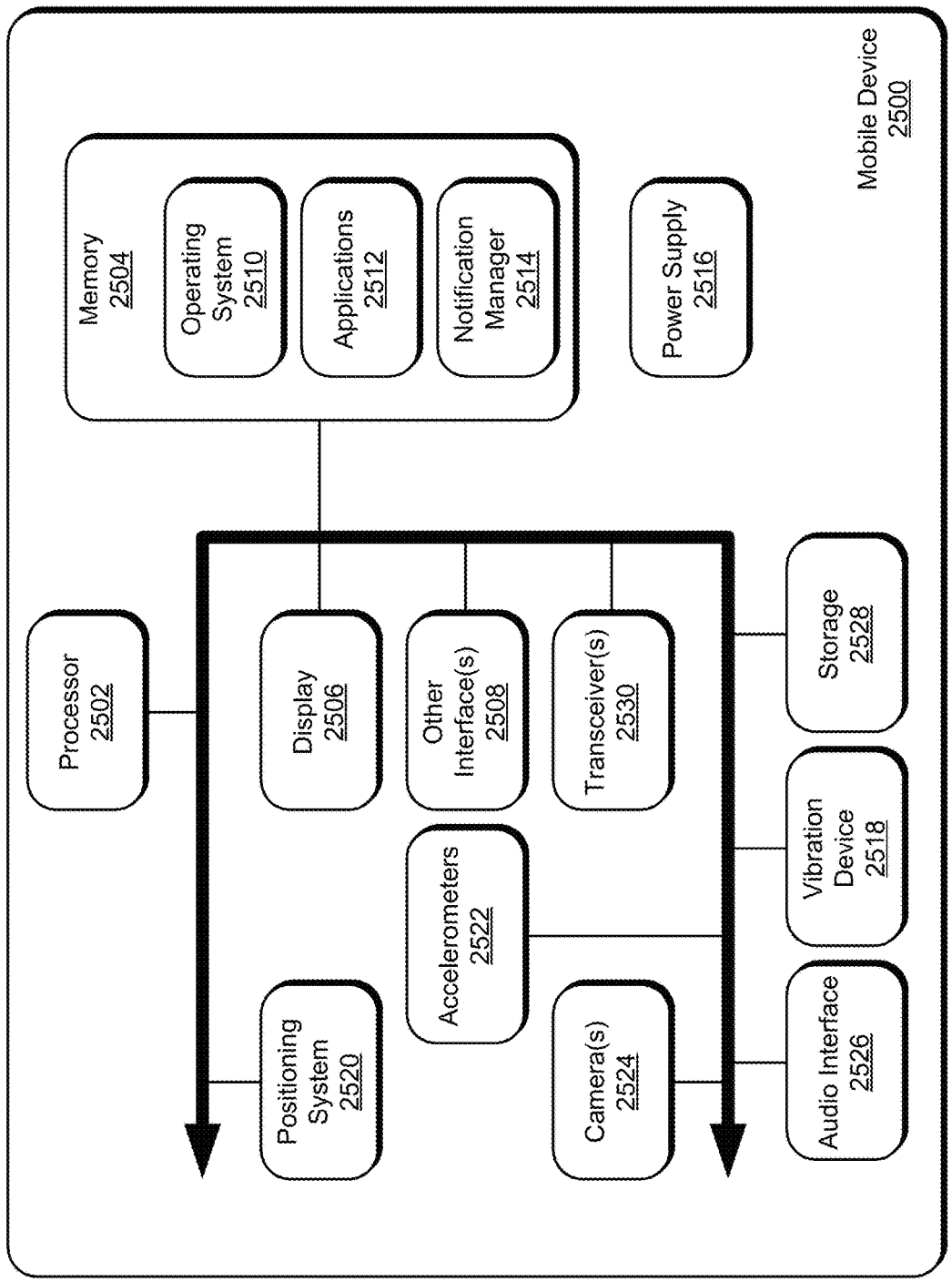
FIG. 25 illustrates an example mobile device that may be used to implement one or more parts of a PCHR system disclosed herein.

FIG. 25 illustrates another example system (labeled as a mobile device 2500) that may be useful in implementing the described PCHR system technology. The mobile device 2500 includes a processor 2502, a memory 2504, a display 2506 (e.g., a touchscreen display), and other interfaces 2508 (e.g., a keyboard). The memory 2504 generally includes both volatile memory (e.g., RAM) and non-volatile memory (e.g., flash memory). An operating system 2510, such as the Microsoft Windows® Phone 25 operating system, the Apple OS®, Android operating system, etc., resides in the memory 2504 and is executed by the processor 2502, although it should be understood that other operating systems may be employed.

One or more application programs 2512 are loaded in the memory 2504 and executed on the operating system 2510 by the processor 2502. Examples of applications 2512 include without limitation email programs, scheduling programs, personal information managers, Internet browsing programs, multimedia player applications, etc. An implementation of the mobile device 2500 may include a mobile PCHR application for the PCHR system disclosed herein, wherein the PCHR application communicates the PCHR system implemented on a cloud server. For example, such PCHR application may be configured to generate a GUI on the mobile device 2500 that provides interactive capabilities to a cardholder using various input modalities (touch, shake, etc.) provided by the mobile device. Furthermore, the PCHR application may also generate a QR code that can be scanned by merchants to complete PCHR transactions.

A notification manager 2514 is also loaded in the memory 2504 and is executed by the processor 2502 to present notifications to the user. For example, when a promotion is triggered and presented to the shopper, the notification manager 2514 can cause the mobile device 2500 to beep or vibrate (via the vibration device 2518) and display the promotion on the display 2506. The mobile device 2500 includes a power supply 2516, which is powered by one or more batteries or other power sources and which provides power to other components of the mobile device 2500. The power supply 2516 may also be connected to an external power source that overrides or recharges the built-in batteries or other power sources.

The mobile device 2500 includes one or more communication transceivers 2530 to provide network connectivity (e.g., mobile phone network, Wi-Fi®, BlueTooth®, etc.). The mobile device 2500 also includes various other components, such as a positioning system 2530 (e.g., a global positioning satellite transceiver), one or more accelerometers 2532, one or more cameras 2534, an audio interface 2526 (e.g., a microphone, an audio amplifier and speaker and/or audio jack), and additional storage 2528. Other configurations may also be employed.

In an example implementation, an electronic health records system, and other modules and services may be embodied by instructions stored in memory 2504 and/or storage devices 2528 and processed by the processing unit 2502. The master pages, the layouts, and other data may be stored in memory 2504 and/or storage devices 2528 as persistent datastores.

Figure 26:
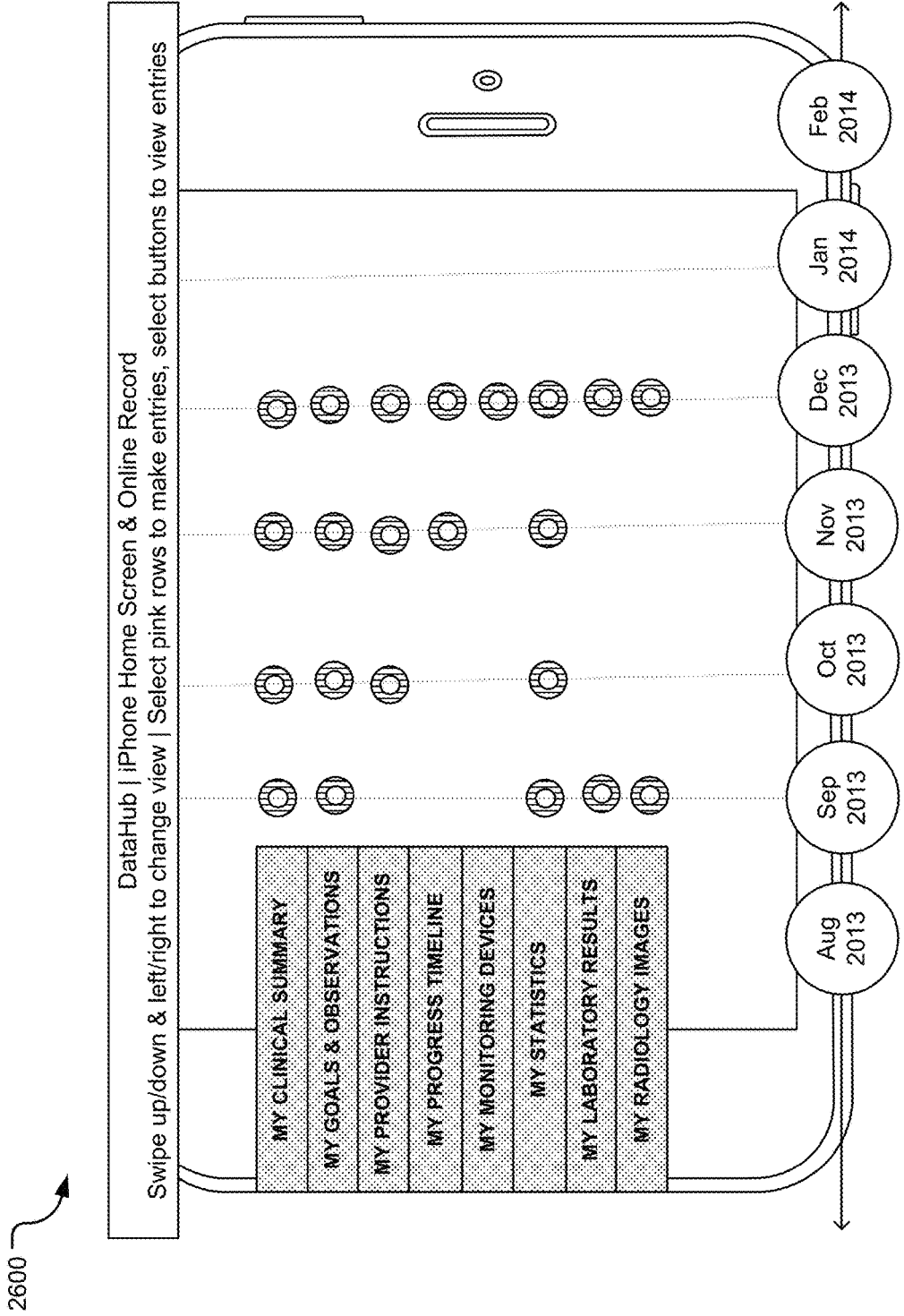
FIG. 26 illustrates an example graphical user interface presented to by the PCHR system disclosed herein that allows a patient to share information, including PCHR patient records, with other users.

FIG. 26 illustrates an example graphical user interface 2600 presented to by the PCHR system disclosed herein that allows a patient to share information, including PCHR patient records, with other users.

Some embodiments may comprise an article of manufacture. An article of manufacture may comprise a tangible storage medium to store logic. Examples of a storage medium may include one or more types of computer-readable storage media capable of storing electronic data, including volatile memory or non-volatile memory, removable or non-removable memory, erasable or non-erasable memory, writeable or re-writeable memory, and so forth. Examples of the logic may include various software elements, such as software components, programs, applications, computer programs, application programs, system programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. In one embodiment, for example, an article of manufacture may store executable computer program instructions that, when executed by a computer, cause the computer to perform methods and/or operations in accordance with the described embodiments. The executable computer program instructions may include any suitable type of code, such as source code, compiled code, interpreted code, executable code, static code, dynamic code, and the like. The executable computer program instructions may be implemented according to a predefined computer language, manner or syntax, for instructing a computer to perform a certain function. The instructions may be implemented using any suitable high-level, low-level, object-oriented, visual, compiled and/or interpreted programming language.

The implementations described herein are implemented as logical steps in one or more computer systems. The logical operations may be implemented (1) as a sequence of processor-implemented steps executing in one or more computer systems and (2) as interconnected machine or circuit modules within one or more computer systems. The implementation is a matter of choice, dependent on the performance requirements of the computer system being utilized. Accordingly, the logical operations making up the implementations described herein are referred to variously as operations, steps, objects, or modules. Furthermore, it should be understood that logical operations may be performed in any order, unless explicitly claimed otherwise or a specific order is inherently necessitated by the claim language.

The above specification, examples, and data provide a complete description of the structure and use of exemplary implementations. Since many implementations can be made without departing from the spirit and scope of the claimed invention, the claims hereinafter appended define the invention. Furthermore, structural features of the different examples may be combined in yet another implementation without departing from the recited claims.

Embodiments of the present technology are disclosed herein in the context of an electronic market system. In the above description, for the purposes of explanation, numerous specific details are set forth in order to provide a thorough understanding of the present invention. It will be apparent, however, to one skilled in the art that the present invention may be practiced without some of these specific details. For example, while various features are ascribed to particular embodiments, it should be appreciated that the features described with respect to one embodiment may be incorporated with other embodiments as well. By the same token, however, no single feature or features of any described embodiment should be considered essential to the invention, as other embodiments of the invention may omit such features.

In the interest of clarity, not all of the routine functions of the implementations described herein are shown and described. It will, of course, be appreciated that in the development of any such actual implementation, numerous implementation-specific decisions must be made in order to achieve the developer's specific goals, such as compliance with application—and business-related constraints, and that those specific goals will vary from one implementation to another and from one developer to another.

According to one embodiment of the present invention, the components, process steps, and/or data structures disclosed herein may be implemented using various types of operating systems (OS), computing platforms, firmware, computer programs, computer languages, and/or general-purpose machines. The method can be run as a programmed process running on processing circuitry. The processing circuitry can take the form of numerous combinations of processors and operating systems, connections and networks, data stores, or a stand-alone device. The process can be implemented as instructions executed by such hardware, hardware alone, or any combination thereof. The software may be stored on a program storage device readable by a machine.

According to one embodiment of the present invention, the components, processes and/or data structures may be implemented using machine language, assembler, C or C++, Java and/or other high level language programs running on a data processing computer such as a personal computer, workstation computer, mainframe computer, or high performance server running an OS such as Solaris® available from Sun Microsystems, Inc. of Santa Clara, Calif., Windows Vista™, Windows NT®, Windows XP PRO, and Windows® 2000, available from Microsoft Corporation of Redmond, Wash., Apple OS X-based systems, available from Apple Inc. of Cupertino, Calif., or various versions of the Unix operating system such as Linux available from a number of vendors. The method may also be implemented on a multiple-processor system, or in a computing environment including various peripherals such as input devices, output devices, displays, pointing devices, memories, storage devices, media interfaces for transferring data to and from the processor(s), and the like. In addition, such a computer system or computing environment may be networked locally, or over the Internet or other networks. Different implementations may be used and may include other types of operating systems, computing platforms, computer programs, firmware, computer languages and/or general purpose machines; and. In addition, those of ordinary skill in the art will recognize that devices of a less general purpose nature, such as hardwired devices, field programmable gate arrays (FPGAs), application specific integrated circuits (ASICs), or the like, may also be used without departing from the scope and spirit of the inventive concepts disclosed herein.

In the context of the present invention, the term "processor" describes a physical computer (either stand-alone or distributed) or a virtual machine (either stand-alone or distributed) that processes or transforms data. The processor may be implemented in hardware, software, firmware, or a combination thereof.

In the context of the present technology, the term "data store," also referred to by the term "repository," describes a hardware and/or software means or apparatus, either local or distributed, for storing digital or analog information or data. The term "data store" describes, by way of example, any such devices as random access memory (RAM), read-only memory (ROM), dynamic random access memory (DRAM), static dynamic random access memory (SDRAM), Flash memory, hard drives, disk drives, floppy drives, tape drives, CD drives, DVD drives, magnetic tape devices (audio, visual, analog, digital, or a combination thereof), optical storage devices, electrically erasable programmable read-only memory (EEPROM), solid state memory devices and Universal Serial Bus (USB) storage devices, and the like. The term "data store" also describes, by way of example, databases, file systems, record systems, object oriented databases, relational databases, SQL databases, audit trails and logs, program memory, cache and buffers, and the like.

The above specification, examples and data provide a complete description of the structure and use of exemplary embodiments of the invention. Although various embodiments of the invention have been described above with a certain degree of particularity, or with reference to one or more individual embodiments, those skilled in the art could make numerous alterations to the disclosed embodiments without departing from the spirit or scope of this invention. In particular, it should be understand that the described technology may be employed independent of a personal computer. Other embodiments are therefore contemplated. It is intended that all matter contained in the above description and shown in the accompanying drawings shall be interpreted as illustrative only of particular embodiments and not limiting. Changes in detail or structure may be made without departing from the basic elements of the invention as defined in the following claims.

What is claimed is:

1. A method of populating an exclusively patient controlled record in a patient controlled electronic health record (PCHR) record repository, the method comprising:
   processing a request from a patient for a health information artifact;
   determining a supplier of the health information artifact;
   generating one or more information request templates required by the supplier of the health information artifact;
   generating an information request document using one or more of the information request templates;
   encrypting the information request document;
   sending the encrypted information request document to the supplier of the health information artifact;
   receiving the health information artifact;
   adding the health information artifact to the exclusively patient controlled record stored in the PCHR record repository; and
   controlling access of a user, human or machine, to the exclusively patient controlled record in the PCHR record repository based on (a) patient authorization of the user for future record access and (b) consent from a registered device in response to the request of a patient-authorized user for current record access, wherein the registered device is a mobile device;
   receiving a request from the user for access to the exclusively patient controlled record in the PCHR record repository;
   determining if the user has previously been authorized by the patient for record access and patient-authorized user permissions associated with the record;
   sending the access request of the patient-authorized user to the registered device; and
   receiving a consent reply from the registered device.

2. The method of claim 1, wherein controlling access to the exclusively patient controlled record in the PCHR record repository further comprises:
   validating the consent reply; and
   if the consent reply is validated, granting user access to the record governed by the patient-authorized permissions.

3. The method of claim 2, wherein validating the consent reply further comprises evaluating a private key and a digital signature received from the registered device.

4. The method of claim 2, wherein the registered device is registered to the patient.

5. The method of claim 2, wherein the registered device is registered to a patient proxy that is designated by the patient.

6. The method of claim 2, further comprising:
   if the consent reply is not validated, denying the user access request, sending an encrypted message including contents of the exclusively patient controlled record to a patient-designated storage device such as the patient registered device, and deleting contents of the exclusively patient controlled record from the PCHR record repository.

7. The method of claim 2, wherein the registered device is a patient registered device, and the method further comprising:

if no consent is received from the patient registered device, communicating the access request to a registered device of a next patient proxy.

8. The method of claim 7, wherein next patient proxy is determined from a patient ordered set of proxies.

9. The method of claim 2, wherein the registered device is a patient registered device and receiving the patient consent further comprises receiving the patient consent from a PCHR app resident on the patient registered mobile device.

10. The method of claim 2, wherein the registered device is a patient registered device, the method further comprising:
receiving a consent from a patient registered device for access by the patient-authorized user to the exclusively patient controlled record in the PCHR record repository;
validating the consent; and
in response to validation of the consent, granting access of the user, consistent with patient-authorized permissions, to the exclusively patient controlled record.

11. The method of claim 10, further comprising:
receiving an annotation to a health information artifact contained in the exclusively patient controlled record in the PCHR record repository without tampering with the original artifact; and
storing an annotated version of the original health information artifact in the exclusively patient controlled record in the PCHR record repository.

12. The method of claim 2, wherein the registered device is a patient registered device and the method further comprising:
receiving a request from the patient registered device authorizing a patient proxy to register a device for managing access, consistent with patient-authorized permissions, to the exclusively patient controlled record in the PCHR record repository, the authorization request further comprising identification of the device of the patient proxy;
validating the authorization request; and
registering the device of the patient proxy as a proxy registered device to manage access to the exclusively patient controlled record in the PCHR record repository.

13. The method of claim 12, wherein the authorization request further comprises a set ordered by the patient of proxies and their proxy registered devices.

14. The method of claim 2, wherein the registered device is a patient registered device and the method further comprising:
determining a security breach at the PCHR record repository; and
in response to the determination of the security breach, sending a notification of the security breach to the patient registered device, transmitting the contents of the exclusively patient controlled record from the PCHR record repository to a patient-selected storage location such as the patient registered device, and deleting all contents of the exclusively patient controlled records from the PCHR record repository.

15. The method of claim 14, further comprising deregistering all proxy registered devices in response to the security breach.

16. One or more tangible computer-readable storage media storing computer executable instructions for performing a computer process on a computing system for populating an exclusively patient controlled record in a patient controlled electronic health record (PCHR) record repository, the computer process comprising:
receiving a request from a patient for a health information artifact;
determining a supplier of the health information artifact;
generating one or more information request templates required by the supplier of the health information artifact;
generating an information request document using one or more of the information request templates;
encrypting the information request document;
sending the encrypted information request document to the supplier of the health information artifact;
receiving the health information artifact;
adding the health information artifact to the exclusively patient controlled record in the PCHR record repository;
storing the updated version of the exclusively patient controlled record in the PCHR record repository; and
controlling access of a user, human or machine, to the exclusively patient controlled record in the PCHR record repository based on patient authorization of a user for future record access and on patient consent from a registered device, wherein the registered device is a mobile device registered by the patient, to the request of a patient-authorized user for current record access.

17. The one or more tangible computer-readable storage media of claim 16, wherein the computer process comprising:
receiving a request from the user for access to the exclusively patient controlled record in the PCHR record repository;
determining if the user has previously been authorized by the patient for record access and patient-authorized user permissions associated with the record;
sending the access request of the patient-authorized user to the registered device;
receiving the consent reply from the registered device;
validating the consent reply; and
if the consent reply is validated, granting the user access to the record governed by the patient-authorized permissions.

18. A patient controlled electronic health record (PCHR) system for populating an exclusively patient controlled record in a patient controlled electronic health record (PCHR) repository, the system comprising one or modules implemented using a hardware processor, the one or more modules comprising:
an interoperability module configured to:
receive a request from a patient-authorized user, human or machine, for a health information artifact,
determine a supplier of the health information artifact,
determine one or more information request templates required by the supplier of the health information artifact,
generate an information request document using one or more of the information request templates,
encrypt the information request document,
communicate the encrypted information request document to the supplier of the health information artifact,
receive the health information artifact,
add the health information artifact to the exclusively patient controlled record in the PCHR record repository, and
store the updated version of the exclusively patient controlled record in the PCHR record repository; and
an access control module configured to control access to the exclusively patient controlled record in the PCHR record repository based on patient authorization of user permissions for future record access and on a consent reply to current record access by the patient-authorized user received from a registered device, wherein the registered device is a mobile device.

19. The patient controlled electronic health record (PCHR) system of claim 18, wherein the access control module is further configured to:
receive a request from a user, human or machine, for access to an exclusively patient controlled record in the PCHR record repository;
determine if the user has been previously authorized by the patient for record access and with what permissions in the hierarchy of patient-authorized user permissions associated with the record;
send the access request of a patient-authorized user to the registered device;
receive a consent reply from the registered device;
validate the consent reply; and
if the consent reply is validated, grant the user access to the exclusively patient controlled record in the PCHR record repository, governed by patient-authorized permissions.

20. The patient controlled electronic health record (PCHR) system of claim 18, further comprising a breach detection module configured to:
detect an episode of unauthorized access to an exclusively patient controlled record in the PCHR record repository;
notify a patient registered device associated with the exclusively patient controlled record of the episode of unauthorized access;
transmit contents of the exclusively patient controlled record from the PCHR record repository to a patient-selected storage location such as the patient registered device; and
delete the contents of the exclusively patient controlled record from the PCHR record repository.

21. The patient controlled electronic health record (PCHR) system of claim 18, further comprising a permissions management module configured to:
assist a patient in creating and managing permissions of an individualized hierarchy of users;
require all authorized human users to be identified as individuals; and
require all authorized machine users to be associated with an individually identified human user.

22. The patient controlled electronic health record (PCHR) system of claim 18, further comprising a proxy management module configured to:
receive an authorization request from a patient registered device authorizing a patient proxy to register a device for managing access to an exclusively patient controlled record in the PCHR record repository, the authorization request further comprising identification of a proxy registered device;
validate the authorization request; and
register the device of the proxy to manage access to the exclusively patient controlled record in the PCHR record repository.

23. The patient controlled electronic health record (PCHR) system of claim 18, further comprising an annotation module configured to:
receive an annotation to a health information artifact contained in the exclusively patient controlled record in the PCHR record repository without tampering with the original artifact; and
store an annotated version of the original health information artifact in the exclusively patient controlled record in the PCHR record repository.

* * * * *